United States Patent
Sakaguchi et al.

(10) Patent No.: US 7,187,746 B2
(45) Date of Patent: Mar. 6, 2007

(54) X-RAY DIAGNOSTIC APPARATUS AND X-RAY IMAGING METHOD

(75) Inventors: Takuya Sakaguchi, Nasushiobara (JP); Satoru Ohishi, Otawara (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 0 days.

(21) Appl. No.: 11/165,463

(22) Filed: Jun. 24, 2005

(65) Prior Publication Data

US 2005/0286679 A1    Dec. 29, 2005

(30) Foreign Application Priority Data

Jun. 25, 2004 (JP) ............................ 2004-187123
May 25, 2005 (JP) ............................ 2005-151846

(51) Int. Cl.
*G01N 23/00* (2006.01)

(52) U.S. Cl. ............................................. 378/8; 378/9

(58) Field of Classification Search ................ 378/4, 378/9, 8, 55, 62, 95, 116, 196–197
See application file for complete search history.

(56) References Cited

U.S. PATENT DOCUMENTS 6,421,412 B1*   7/2002   Hsieh et al. ................... 378/9
2002/0118790 A1*   8/2002   Pan et al. ...................... 378/8

FOREIGN PATENT DOCUMENTS

JP             10-234717         9/1998

* cited by examiner

*Primary Examiner*—Edward J. Glick
*Assistant Examiner*—Hoon Song
(74) *Attorney, Agent, or Firm*—Oblon, Spivak, McClelland, Maier & Neustadt, P.C.

(57) ABSTRACT

Projection data are obtained by using a method for imaging by rotating the first imaging system having an X-ray generating unit $1a$ and the second imaging system having an X-ray generating unit $1b$. The obtained projection data are subjected to a reconstruction process to generate X-ray image data. In this case, a relative angle $\eta 0$ formed between the imaging systems is setup according to a palmic period $T0$ of a subject and a rotation velocity $Vr$ of the imaging systems. Thus, the projection data from more directions at a predetermined palmic time-phase are collected without overlapping.

14 Claims, 15 Drawing Sheets

X-RAY DIAGNOSTIC APPARATUS AND X-RAY IMAGING METHOD

BACKGROUND OF THE INVENTION

1. Field of the Invention

The present invention relates to an X-ray diagnostic apparatus and an X-ray imaging method, and more particularly, to an X-ray diagnostic apparatus and an X-ray imaging method, in which reconstruct projection data obtained by rotating X-ray generating units and X-ray detecting units to generate X-ray image data.

2. Description of the Related Art

Medical image diagnostic technology using an X-ray diagnostic apparatus, an MRI (magnetic resonance imaging) apparatus, or an X-ray CT (computed tomography) apparatus has made considerable strides since computer technology progressed during the 1970s. The medical image diagnostic technology is now indispensable to current medical treatment.

In recent years, following the progress of catheterization, X-ray diagnoses have been advancing mainly in the cardiological field. A typical X-ray diagnostic apparatus for a cardiological diagnosis includes an X-ray generating unit, an X-ray detecting unit, a member holding those units, a bed (table), and a signal processing unit. The holding member includes a C-shaped arm or an Ω-shaped arm. The holding member is combined with the bed including a cantilever table such that a patient (hereinafter, referred to as a subject) can be subjected to X-ray imaging at the optimum position or angle.

In the X-ray diagnostic apparatus, the X-ray detecting unit generally includes an X-ray film or an I. I. (X-ray image intensifier) as a detector. According to an X-ray imaging method using the I. I., X-rays generated from an X-ray tube in the X-ray generating unit are exposed to a subject. X-ray projection data (hereinafter, referred to as projection data) obtained from X-rays passed through the subject is converted into an optical image. The optical image is captured by an X-ray TV camera and the captured image is converted into electric signals. The electric signals are converted into digital signals and the resultant signals are displayed in a monitor. Therefore, the imaging method using the I. I. realizes real-time imaging which is impossible by an imaging method using a film. In addition, since projection data can be collected as digital signals, various kinds of imaging processing can be performed.

In recent years, attention has been given to two-dimensional array type planar detectors instead of the I. I. and some of the detectors are in practical use. According to a proposed method, an X-ray generating unit having such a planar detector and an X-ray detecting unit are fixed to a holding member (C-shaped arm) such that the units face each other and projection data is collected while the units are being rotated about the axis which is substantially parallel to the body axis of a subject (see, for example, JP-A-2002-263093).

According to the method presented in JP-A-2002-263093, the rotating X-ray generating unit sequentially exposes X-ray cone beams (three-dimensionally confined beams) to the subject at some angles. The planar detector in the X-ray detecting unit, arranged opposite to the X-ray generating unit with the subject therebetween, detects the amount of X-rays passed through the subject. Projection data is generated on the basis of the detected amount of X-rays. Further, the projection data is subjected to a reconstruction process, thus generating three-dimensional data (hereinafter, referred to as volume data).

According to another proposed method, a plurality of imaging systems each having an X-ray generating unit and an X-ray detecting unit are used (see, for example, JP-A-H10-234717). The imaging systems are simultaneously rotated about a subject, thus resulting in a reduction in time to collect projection data.

In the foregoing X-ray diagnostic apparatus, the rotational velocity of an imaging system is generally 40 degrees/second or 60 degrees/second. Assuming that the fan angle is, e.g., 20 degrees, time required for rotation by (180 degrees+fan angle) is in the range of three to five seconds. It is assumed that projection data regarding the heart of the subject is collected in the rotational range of (180 degrees+fan angle) using the imaging system having the above rotational velocity. Since heart rate is once per second or twice per second, the heart pulsates three or ten times for a period during which the imaging system rotates in the rotational range.

Since the rotational velocity of the imaging system is not sufficiently higher than the heart rate, projection data is collected in different palmic time-phases. When the collected projection data is subjected to the reconstruction process to obtain volume data, disadvantageously, the volume data includes an artifact which is caused by the motion of the heart. The foregoing JP-A-2002-263093 and JP-A-H10-234717 do not describe a method for overcoming the above-mentioned disadvantage.

As methods for imaging a rhythmically pulsating organ, such as a heart, ECG gating methods have been known: Projection data is collected at the end of diastole (end-diastole) or the end of systole (end-systole) during which the motion of the organ is relatively small, so that reconstructed image data can be generated with high quality.

A period corresponding to end-diastole or end-systole, during which the motion of the heart is small, is approximately 30% of the palmic cycle. Projection data cannot be collected for the remaining period corresponding to 70% of the palmic cycle. Therefore, the reconstruction process is performed on the basis of projection data obtained at restricted angles. Consequently, a serious artifact occurs in obtained volume data, thus significantly reducing the diagnostic ability of the apparatus.

FIGS. 17 to 19 are diagrams explaining the above disadvantages. FIG. 17 is a diagram showing data collection timings in collecting projection data according to a conventional ECG gating method. FIG. 18 is a diagram showing the positional relationship between an X-ray generating unit and an X-ray detecting unit in collecting projection data according to the conventional ECG gating method shown in FIG. 17. FIG. 19 is a diagram showing X-ray exposure positions in collecting projection data according to the conventional ECG gating method shown in FIG. 17.

FIG. 17 shows X-ray exposure timings t1 to t3 at end-diastole time T11, those t4 to t6 at end-diastole time T12, and those t7 to t9 at end-diastole time T13, the end-diastole times T11 to T13 being set based on R waves R1, R2, R3, . . . of electrocardiographic waves (hereinafter, referred to as ECG signals).

The X-ray generating unit and the X-ray detecting unit are provided for an imaging system of an X-ray diagnostic apparatus such that the units face each other with a subject therebetween as shown in FIG. 18 and rotates about the subject at a predetermined velocity. As shown in FIG. 18, in each of X-ray exposure positions A1 to A3, the X-ray generating unit emits X-rays toward the X-ray detecting unit which is opposite to the X-ray exposure position. The X-ray exposure positions A1 to A3 correspond to X-ray exposure timings t1 to t3 in FIG. 17, respectively.

Similarly, as shown in FIG. 19, the X-ray generating unit emits X-rays toward the X-ray detecting unit in each of X-ray exposure positions A4 to A9. The X-ray exposure positions A4 to A6 correspond to X-ray exposure timings t4 to t6 at end-diastole time T12, respectively. The X-ray exposure positions A7 to A9 correspond to X-ray exposure timings t7 to t9 at end-diastole time T13, respectively.

Assuming that the fan angle $\phi 0$ is 20 degrees, a rotational range $\theta 0$ necessary to collect projection data is 200 degrees. Projection data at end-diastole is collected in a range corresponding to approximately 30% of the rotational range $\theta 0$. Therefore, on the condition that projection data is collected while the imaging system is being rotated every angle of, e.g., 1 degree, 60 pieces of projection data are collected in the rotational range $\theta 0$. In other words, when projection data at end-diastole is collected and the reconstruction process is performed on the basis of the collected projection data, the amount of data is drastically reduced. In addition, those pieces of projection data are obtained at irregular intervals. Thus, an unacceptable artifact occurs in volume data obtained by the reconstruction process or image data.

SUMMARY OF THE INVENTION

Accordingly, the present invention has been made in light of the conventional situations, and it is an object of the present invention to provide an X-ray diagnostic apparatus and an X-ray imaging method in which make it possible to collect projection data on a predetermined time-phase of palmus from more directions by using a plurality of imaging systems and to perform reconstruct process for the obtained projection data to generate X-ray image data with high image quality.

In an aspect, to achieve the object, the present invention provides an X-ray diagnostic apparatus comprising a palmic information collecting unit collecting a palmic information of a subject, imaging units irradiating and detecting X-rays respectively to the subject on a predetermined time-phase of the palmic information to collect projection data, an imaging system moving unit moving the imaging units respectively around the subject, an imaging system motion control unit controlling motions of the imaging units respectively and an image data generating unit performing a reconstruction process to the projection data to generate X-ray image data.

Furthermore, the present invention provides an X-ray diagnostic apparatus comprising imaging units irradiating and detecting X-rays respectively to a subject to collect projection data, an imaging system moving unit moving the imaging units respectively with a same velocity substantially around the subject, an imaging system motion control unit set up a relative angle formed by the imaging units according to the same velocity and an image data generating unit performing a reconstruction process to the projection data to generate X-ray image data.

On the other hand, the present invention provides an X-ray imaging method comprising collecting a palmic information of a subject, controlling movements of imaging units around the subject to collect projection data at a predetermined time-phase on the palmic information and performing a reconstruction process to the projection data to generate X-ray image data.

Furthermore, the present invention provides an X-ray imaging method comprising collecting a palmic information of a subject, setting up a relative angle formed by imaging units arranged around the subject according to the palmic information and moving velocities of the imaging units, collecting projection data at a predetermined time-phase on the palmic information, moving the imaging units around the subject and performing a reconstruction process to the projection data to generate X-ray image data.

In the present invention, it is possible to collect projection data on a predetermined time-phase of palmus efficiently from more and to perform reconstruction process for these projection data directions to generate high quality of image data.

DESCRIPTION OF THE PREFERRED EMBODIMENTS

The present invention will now be described in further detail below with reference to embodiments in conjunction with the accompanying drawings.

The characteristic features of an embodiment, which will be described below, of the present invention are that the present invention is applied to a biplane type X-ray diagnostic apparatus having two imaging systems and a relative angle defined by the crossing angle between the imaging central axes (each axis formed between the center of an X-ray generating unit and the center of the corresponding X-ray detecting unit) of the two imaging systems is set based on palmic information obtained from a subject.

1. Constitution

Figure 1:
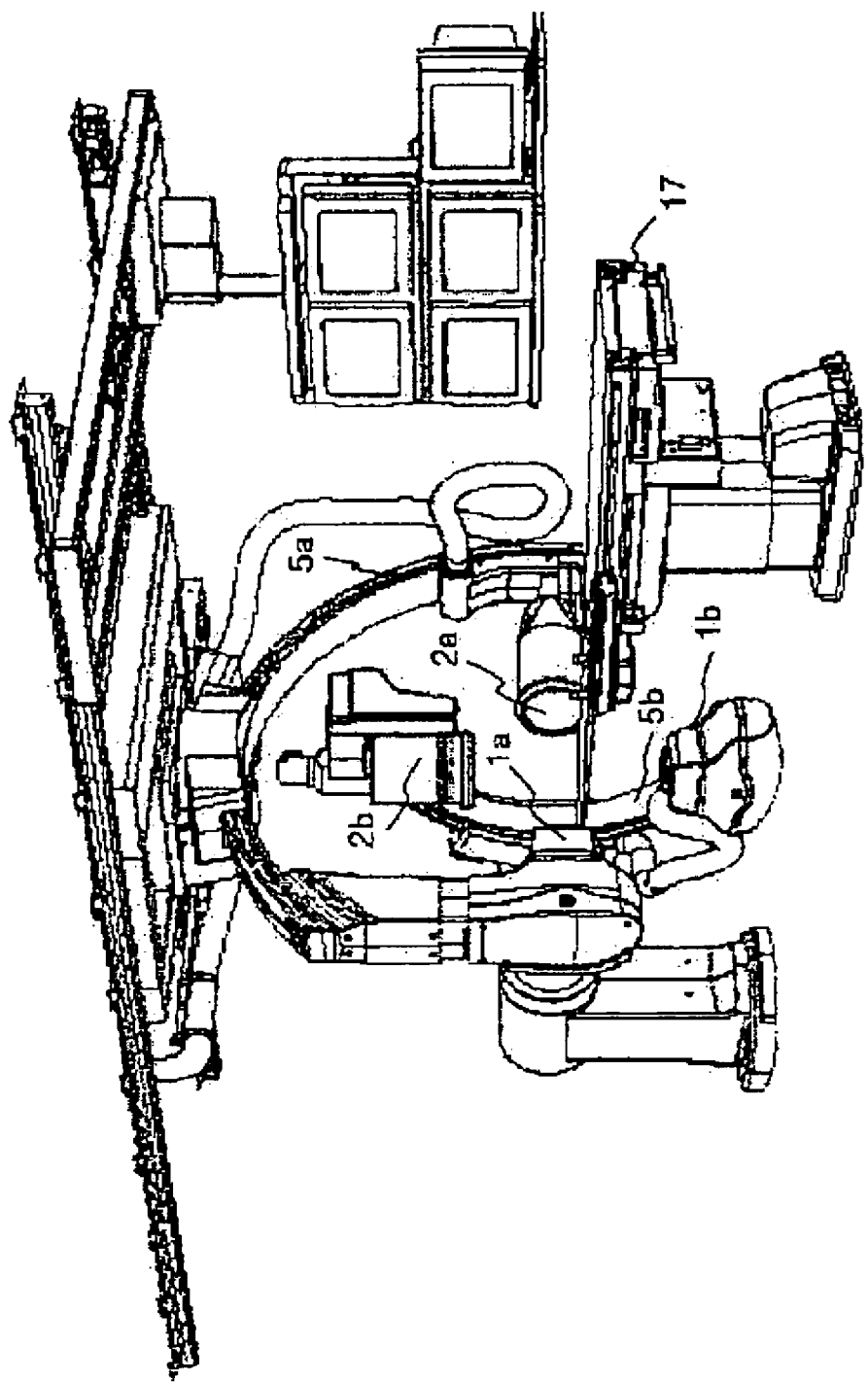
FIG. 1 is a diagram showing imaging systems of an X-ray diagnostic apparatus according to the embodiment of the present invention.
Figure 2:
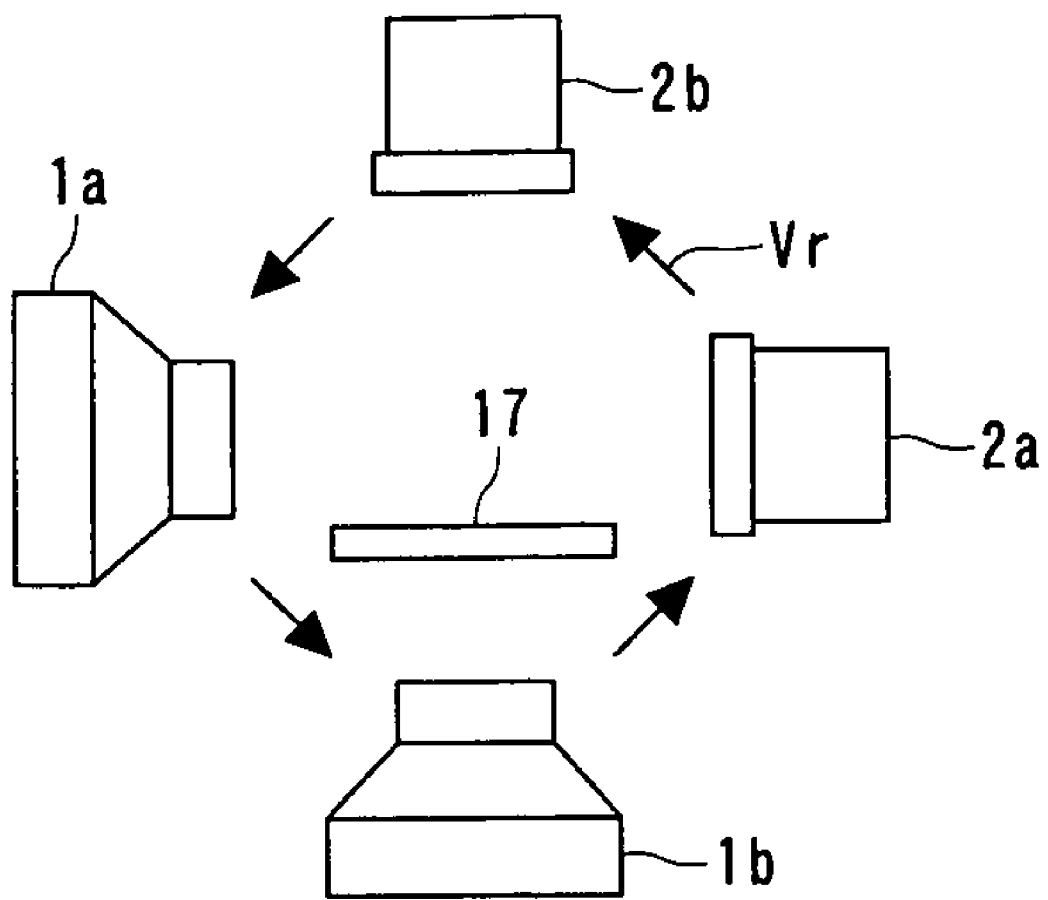
FIG. 2 is a diagram showing the rotation direction of the imaging systems shown in FIG. 1.
Figure 3:
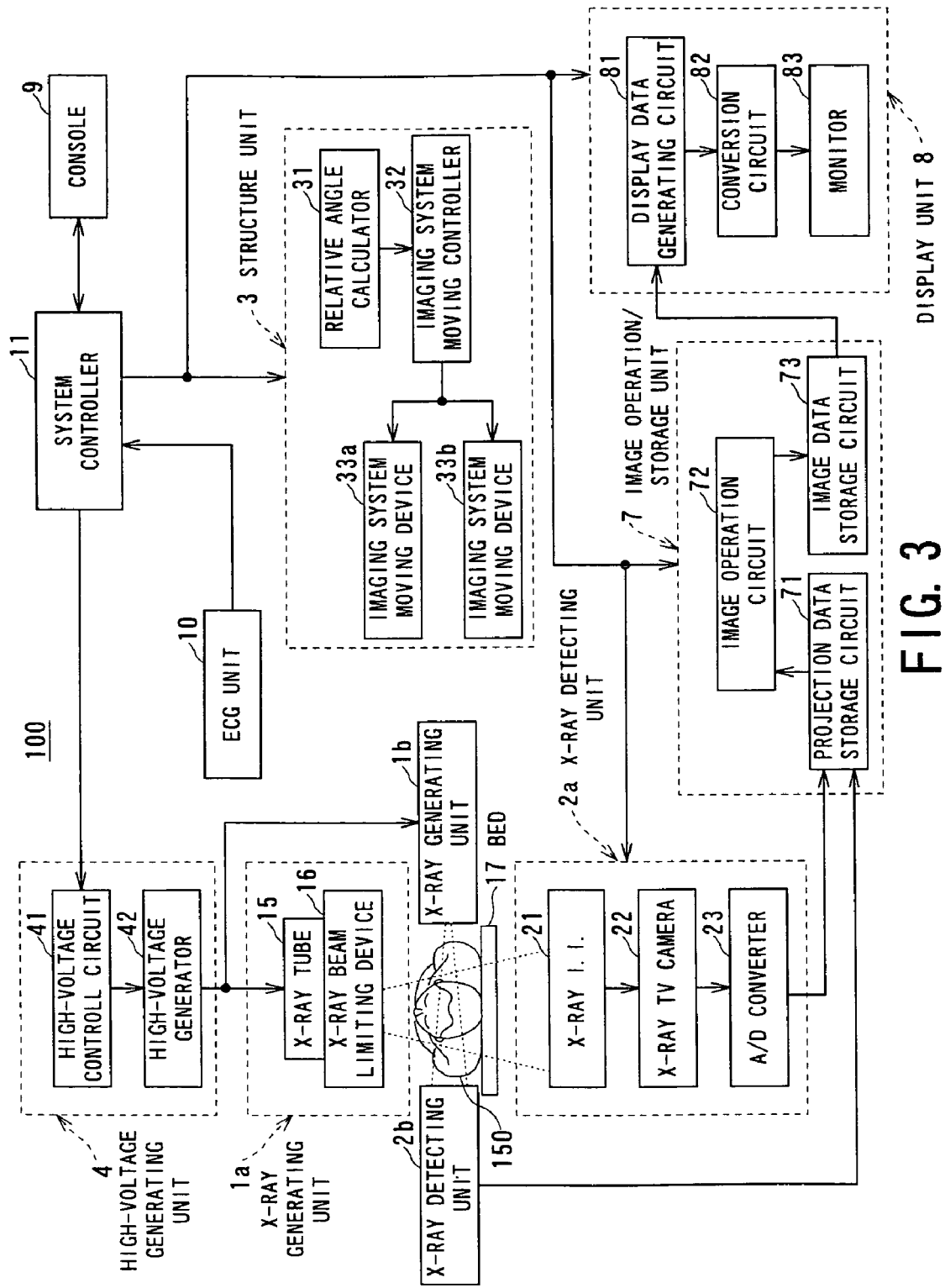
FIG. 3 is a block diagram of the structure of the X-ray diagnostic apparatus in FIG. 1.

A constitution for an X-ray diagnostic apparatus of an embodiment according to the present invention will be described with reference to form FIG. 1 to FIG. 11. FIG. 1 is a diagram showing imaging systems of an X-ray diagnostic apparatus according to the embodiment of the present invention. FIG. 2 is a diagram showing the rotation direction of the imaging systems shown in FIG. 1. FIG. 3 is a block diagram of the structure of the X-ray diagnostic apparatus 100 in FIG. 1.

According to the present embodiment, the X-ray diagnostic apparatus 100 includes a first imaging system and a second imaging system. The first imaging system has an X-ray generating unit 1a and an X-ray detecting unit 2a, which face each other with a subject (not shown) on a bed 17 therebetween as shown in FIG. 1. The second imaging system has an X-ray generating unit 1b and an X-ray detecting unit 2b which similarly face each other with the subject on the bed 17 therebetween. The X-ray generating unit 1a and the X-ray detecting unit 2a are respectively fixed in the vicinities of both ends of a first holding member (holding arm) 5a which is independent of the second holding member 5b about movement. The X-ray generating unit 1b and the X-ray detecting unit 2b are respectively fixed in the vicinities of both ends of a second holding member 5b. As shown in FIG. 2, the first and second imaging systems rotate at a predetermined rate Vr in the same plane substantially perpendicular to the longitudinal direction of the bed 17.

Referring to FIG. 3, the X-ray diagnostic apparatus 100 includes the X-ray generating units 1a and 1b, a high-voltage generating unit 4, the X-ray detecting units 2a and 2b, the first and second holding members 5a and 5b (not shown), and a structure unit 3. The X-ray generating units 1a and 1b apply X-rays to a subject 150. The high-voltage generating unit 4 supplies high voltage necessary for X-ray exposure to the X-ray generating units 1a and 1b. The X-ray detecting units 2a and 2b detect projection data passed through the subject 150. The first holding member 5a holds the X-ray generating unit 1a and the X-ray detecting unit 2a. The second holding member 5b holds the X-ray generating unit 1b and the X-ray detecting unit 2b. The structure unit 3 moves the first and second holding members 5a and 5b and rotates the X-ray generating units 1a and 1b and the X-ray detecting units 2a and 2b about the subject 150.

In addition, the X-ray diagnostic apparatus 100 includes an image operation/storage unit 7, a display unit 8, a console 9, an ECG unit 10, and a system controller 11. The image operation/storage unit 7 performs a reconstruction process to the projection data detected by the X-ray detecting units 2a and 2b to generate volume data and further generates three-dimensional image data or two-dimensional image data, such as MPR (Multi-Planar Reconstruction) image data on the basis of the volume data. The display unit 8 displays image data. The console 9 is used to input subject information and various commands, set imaging conditions, and select an image display mode. The ECG unit 10 collects ECG signals from the subject 150. The system controller 11 controls the above-mentioned units.

Each of the X-ray generating units 1a and 1b includes an X-ray tube 15 for applying X-rays to the subject 150 and an X-ray beam limiting device 16 for shaping the X-rays generated from the X-ray tube 15 into an X-ray cone (cone beams). The X-ray tube 15 is a vacuum tube for generating X-rays by accelerating electrons emitted from a cathode (filament) at high voltage to strike a tungsten anode. The X-ray beam limiting device 16 is arranged between the X-ray tube 15 and the subject 150. The X-ray beam limiting device 16 has a function for limiting the X-ray beams generated from the X-ray tube 15 to an exposure range of a predetermined size in the corresponding X-ray detecting unit 2.

The X-ray detecting units 2a and 2b can include a system using an X-ray I. I., described above, serving as an example of two-dimensional X-ray detectors or a system using two-dimensionally arrayed X-ray detecting elements, i.e., a planar X-ray detector (two-dimensional array type X-ray detector).

Figure 4:
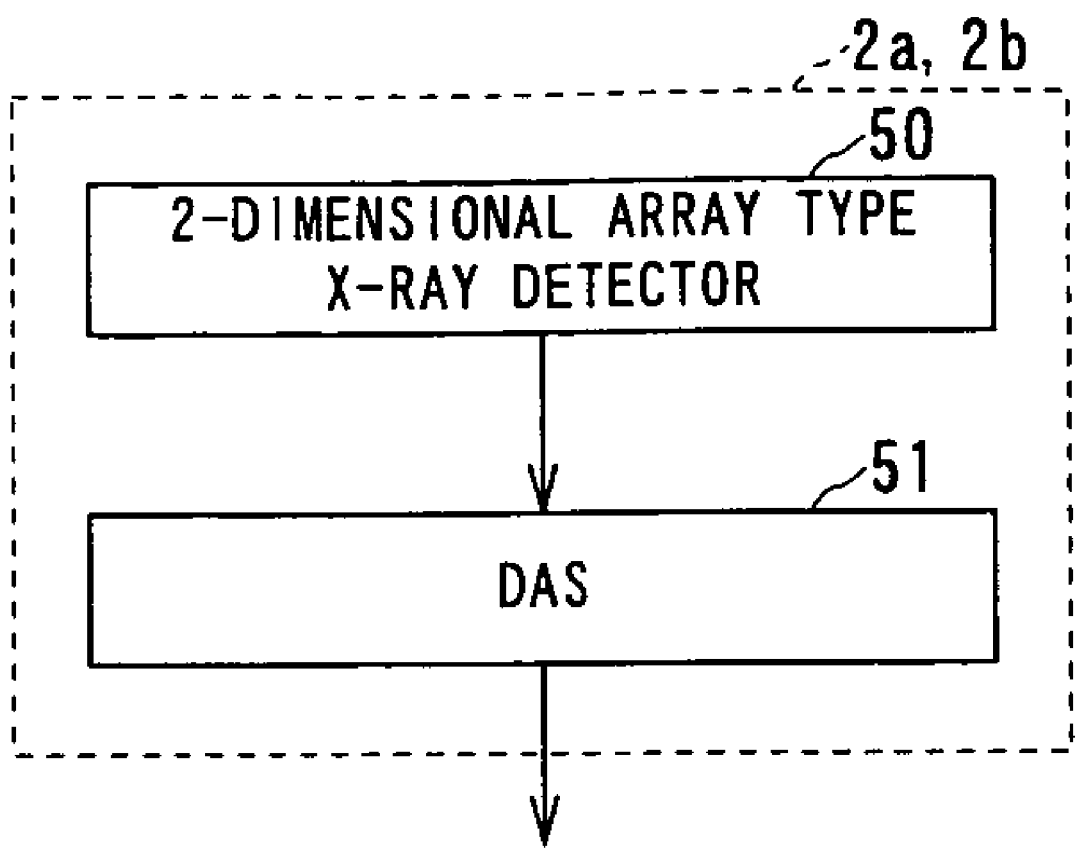
FIG. 4 is a diagram showing an example of the structure of each of the X-ray detecting units in FIG. 3, which has a two-dimensional array type X-ray detector.

FIG. 4 is a diagram showing an example of the structure of each of the X-ray detecting units 2a and 2b in FIG. 3, which has a two-dimensional array type X-ray detector.

Referring to FIG. 4, each of the X-ray detecting units 2a and 2b can include a two-dimensional array type X-ray detector 50 and a DAS (data acquisition system) 51 as is general knowledge. The two-dimensional array type X-ray detector 50 detects X-rays through two-dimensionally arranged detecting elements and converts the X-rays into electric signals. The DAS 51 collects X-ray detection data detected as electric signals through the respective detecting elements and performs necessary processes, e.g., A/D conversion and logarithmic transformation, to the collected data, thus generating projection data.

In the following description, it is assumed that each of the X-ray detecting units 2a and 2b includes the system using the X-ray I. I. The structure of each of the X-ray detecting units 2a and 2b is not limited to the system. Other systems, e.g., the system using the two-dimensional array type X-ray detector 50 as shown in FIG. 4 can be used.

In other words, each of the X-ray detecting units 2a and 2b includes an X-ray I. I. 21, an X-ray TV camera 22, and an A/D converter 23. The X-ray I. I. 21 transforms X-rays passed through the subject 150 into visible light. In addition, the X-ray I. I. 21 intensifies the brightness of light during the transformation from light to electrons to light, thus generating high-sensitive projection data. On the other hand, the X-ray TV camera 22 converts the above-mentioned optical projection data into electric signals using a CCD (Charge Coupled Device) imaging element. The A/D converter 23 converts time-series electric signals (video signals) generated from the X-ray TV camera 22 into digital signals.

The structure unit 3 includes a relative angle calculator 31 for calculating an angle (relative angle) $\eta 0$, which the central axis of the first imaging system having the X-ray generating unit 1a and the X-ray detecting unit 2a forms with that of the second imaging system having the X-ray generating unit 1b and the X-ray detecting unit 2b, on the basis of a palmic cycle T0 obtained from the subject 150 and the angular rate of rotation (hereinafter, referred to as a rotational velocity) Vr of each of the imaging systems.

The structure unit 3 further includes an imaging system moving controller 32 and imaging system moving devices 33a and 33b. The imaging system moving controller 32 sets an initial position of each of the first and second imaging systems on the basis of the relative angle calculated by the relative angle calculator 31. In addition, the imaging system moving controller 32 generates moving control signals to rotate the first and second imaging systems at the predetermined rotational velocity Vr while the relative angle $\eta 0$ between the imaging systems is maintained. The imaging system moving devices 33a and 33b rotate the first and second imaging systems about the subject on the basis of the moving control signals, respectively. The imaging system moving controller 32 has a function of supplying information regarding the position (hereinafter, referred to as a rotational position) of each rotating imaging system to the system controller 11, which will be described hereinafter.

The imaging system moving controller 32 supplies control signals to move the first and second imaging systems along the body axis of the subject 150 to the imaging system moving devices 33a and 33b in accordance with a control signal supplied from the system controller 11. The imaging system moving devices 33a and 33b move the first and second imaging systems along the body axis on the basis of the control signals, respectively. Thus, the position of a cross-sectional plane where projection data is collected can be set or updated. An explanation regarding the movements of the imaging systems along the body axis will be omitted.

Figure 5:
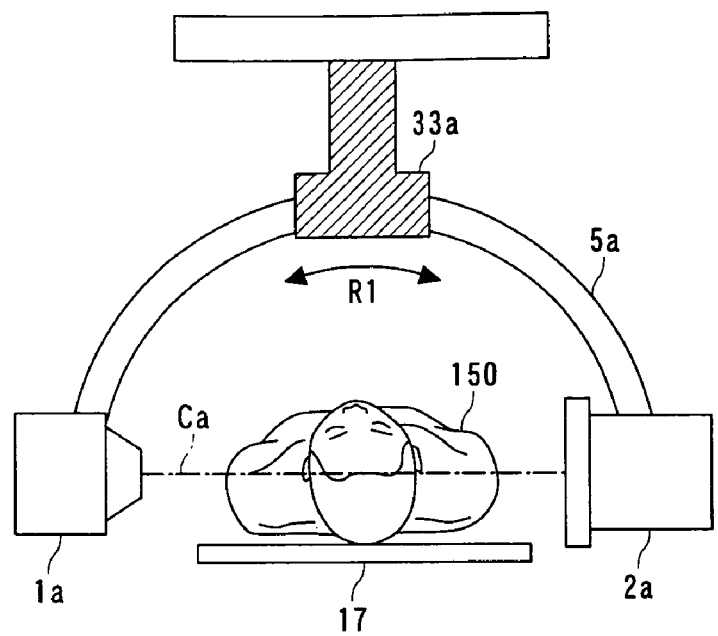
FIG. 5 is a diagram showing the rotation directions of one side of the X-ray generating unit and the X-ray detecting unit shown in FIG. 1.
Figure 6:
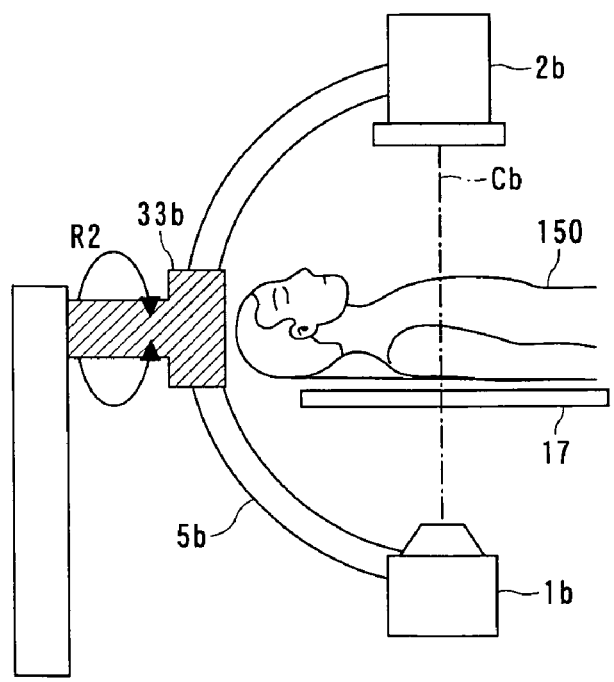
FIG. 6 is a diagram showing the rotation directions of the other side of the X-ray generating unit and the X-ray detecting unit shown in FIG. 1

FIG. 5 is a diagram showing the rotation directions of one side of the X-ray generating unit 1a and the X-ray detecting unit 2a shown in FIG. 1. FIG. 6 is a diagram showing the rotation directions of the other side of the X-ray generating unit 1b and the X-ray detecting unit 2b shown in FIG. 1.

In other words, FIG. 5 shows the X-ray generating unit 1a and the X-ray detecting unit 2a rotated by the imaging system moving device 33a. The imaging system moving device 33a, attached to a ceiling, rotates the X-ray generating unit 1a and the X-ray detecting unit 2a in any one of the directions R1 about the axis which is substantially parallel to the body axis of the subject 150. On the other hand, FIG. 6 shows the X-ray generating unit 1b and the X-ray detecting unit 2b rotated by the imaging system moving device 33b. The imaging system moving device 33b, attached to a floor-standing gantry, rotates the X-ray generating unit 1b and the X-ray detecting unit 2b in any one of the directions R2 about the axis which is substantially parallel to the body axis of the subject 150.

Figure 7:
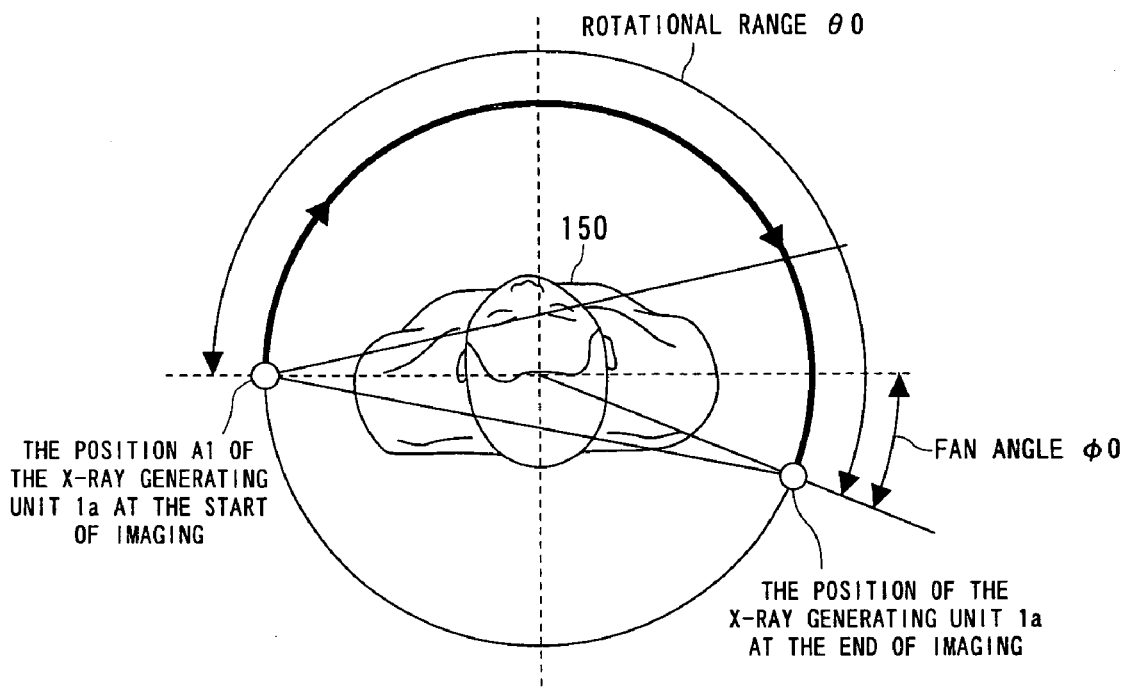
FIG. 7 is a diagram showing a rotational range of the X-ray generating unit 1a shown in FIG. 1.

FIG. 7 is a diagram showing a rotational range of the X-ray generating unit 1a shown in FIG. 1.

FIG. 7 shows a rotational range $\theta 0$ of the X-ray generating unit 1a in collecting the minimum amount of projection data required to the reconstruction process. In the collection of projection data for image reconstruction, generally, the minimum rotational range $\theta 0$ of the X-ray generating unit 1a is expressed by (180 degree+fan angle $\phi 0$). As shown in FIG. 7, the fan angle $\phi 0$ is determined by the radiation angle of X-rays radiated from the X-ray generating unit 1a. The X-ray generating unit 1a and the X-ray detecting unit 2a (not shown) are rotated in the rotational range $\theta 0$, so that projection data can be collected at 180 degrees necessary for the reconstruction process regarding a region of interest of the subject 150.

In FIGS. 1, 5, and 6, the relative angle which the central axis Ca of the first imaging system having the X-ray generating unit 1a and the X-ray detecting unit 2a forms with the central axis Cb of the second imaging system having the X-ray generating unit 1b and the X-ray detecting unit 2b is approximately 90 degrees. As already described above, the relative angle can be arbitrarily set based on palmic information of the subject 150. A process of setting the relative angle based on palmic information is of primary importance in the present embodiment. The process will be described in detail hereinafter.

Again referring to FIG. 3, the high-voltage generating unit 4 includes a high-voltage generator 42 and a high-voltage control circuit 41. In order to accelerate thermal electrons emitted from the cathode of the X-ray tube 15, the high-voltage generator 42 generates high voltage to be applied between the anode and the cathode. In accordance with an instruction signal generated from the system controller 11, the high-voltage control circuit 41 controls X-ray exposure conditions, such as tube current, tube voltage, and X-ray exposure time in the high-voltage generator 42.

On the other hand, the image operation/storage unit 7 includes a projection data storage circuit 71, an image operation circuit 72, and an image data storage circuit 73. The first and second imaging systems are rotated about the subject to perform X-ray imaging. Projection data obtained through the X-ray detecting units 2a and 2b is temporarily stored in the projection data storage circuit 71 together with imaging positional information (i.e., information regarding the rotational positions of the X-ray generating units 1a and 1b).

The image operation circuit 72 reads out the stored projection data of the subject 150 and the rotational position information from the projection data storage circuit 71 and performs the reconstruction process based on the read data to generate volume data. In addition, the image operation circuit 72 generates desired three-dimensional image data or two-dimensional image data using the obtained volume data. The image data storage circuit 73 stores the three-dimensional image data or two-dimensional image data generated by the image operation circuit 72. A method for generating the volume data is known as an image reconstruction method for X-ray CT apparatuses. A detailed description of the method will be omitted.

On the basis of the volume data, the image operation circuit 72 generates three-dimensional image data according to, e.g., a volume rendering method or two-dimensional image data according to an MPR method or an MIP (Maximum-Intensity-Projection) method.

The display unit 8 displays the above-mentioned image data stored in the image data storage circuit 73 of the image operation/storage unit 7. The display unit 8 includes a display data generating circuit 81, a conversion circuit 82, and a monitor 83. The display data generating circuit 81 combines the image data with numerals and/or characters, serving as attached information to generate the combined data as display image data. The conversion circuit 82 performs D/A conversion and TV format conversion to the display image data to generate video signals. The monitor 83 displays the video signals.

The console 9 is an interactive interface including input devices, such as a keyboard, a track ball, a joystick, and a mouse, a display panel, and various switches. The console 9 is used to enter subject information and various commands and to select the optimum X-ray exposure conditions suitable for an organ to be imaged, imaging conditions, e.g., the rotational velocity and the imaging position of each imaging system, and a set image display mode. The X-ray exposure conditions include tube voltage and tube current to be applied to the X-ray tube 15 and X-ray exposure time. Image display modes includes a three-dimensional image display mode, an MIP image display mode, and an MPR image display mode.

The ECG unit 10 receives ECG signals detected by electrodes (not shown) attached to the chest of the subject 150 and then converts the received signals into digital signals.

The system controller 11 includes a CPU (Central Processing Unit) and a storage circuit which are not shown. The storage circuit stores the above-mentioned various pieces of information entered or set in the console 9 by an operator. On the basis of the information, the CPU controls the high-voltage generating unit 4, the X-ray detecting units 2a and 2b, the structure unit 3, the image operation/storage unit 7, and the display unit 8 and also controls the whole X-ray diagnostic apparatus.

In particular, according to the present embodiment, in order to set the relative angle η0 between the first and second imaging systems, the system controller 11 supplies the ECG signals of the subject 150, supplied from the ECG unit 10, and the preset rotational velocity Vr of each imaging system to the relative angle calculator 31 in the structure unit 3.

In addition, the system controller 11 previously determines a plurality of X-ray exposure positions of, e.g., the X-ray generating unit 1a. When the X-ray exposure positions agree with the rotational position information of the X-ray generating unit 1a supplied from the imaging system moving controller 32 in the structure unit 3, the system controller 11 supplies a drive signal for X-ray exposure to the high-voltage control circuit 41 in the high-voltage generating unit 4.

Next, the process of setting the relative angle η0 between the first and second imaging systems will now be described with reference to FIGS. 8 to 10. The structure unit 3 performs the process.

Figure 8:
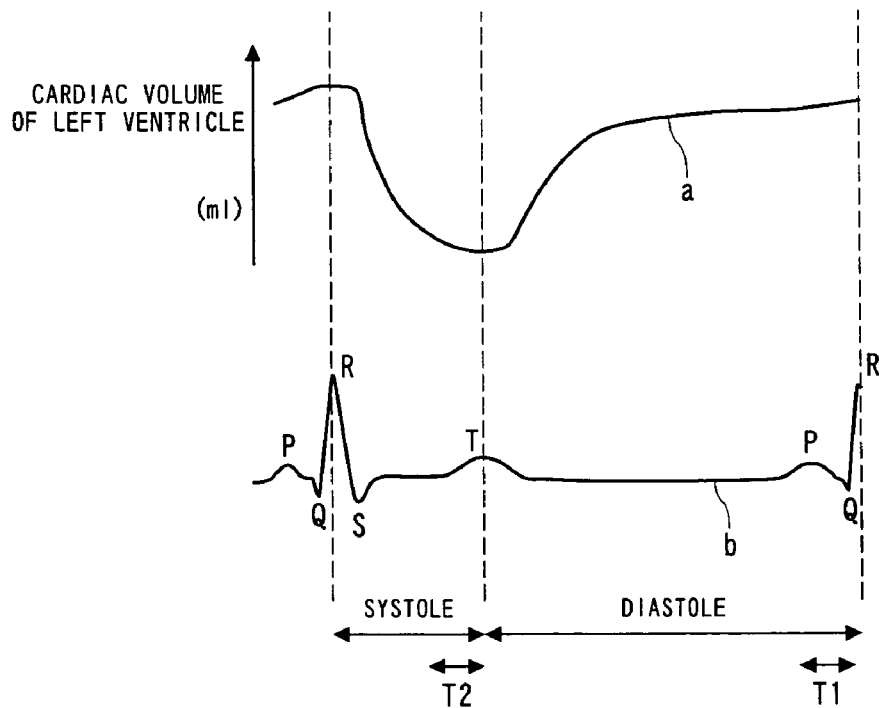
FIG. 8 is a diagram showing a curve indicating a change in cardiac volume of the left ventricle in systole and diastole of the palmic cycle and ECG signals.

FIG. 8 is a diagram showing a curve indicating a change in cardiac volume of the left ventricle in systole and diastole of the palmic cycle and ECG signals. FIG. 9 is a diagram showing the relationship between palmic time-phase and the rotational positions of the X-ray generating units provided for the two imaging systems in FIG. 1 when the relative angle between the imaging systems is optimized. FIG. 10 is a diagram showing the rotational positions of the X-ray generating units of the two imaging systems in FIG. 1 when the relative angle between the imaging systems is optimized.

As described above, it is preferable to collect projection data when the motion of a periodically pulsating organ is relatively small, i.e., at the end of systole or diastole. FIG. 8 shows a curve a indicating a change in volume of the left ventricle and ECG signals b. With respect to the ECG signals, the interval between a first R wave and a T wave corresponds to systole and that between the T wave and the next R wave corresponds to diastole. The change on the cardiac volume of the left ventricle is minimized at time T1 of end diastole and at time T2 of end systole.

In other words, the projection data collected at end-diastole time T1 or end-systole time T2 when the motion of the heart is minimized is subjected to the reconstruction process, so that volume data or image data, in which the influence of the motion is minimized, can be generated with high quality. Collecting projection data at end-diastole time T1 will now be described below. Data can also be collected at end-systole time T2.

Figure 9:
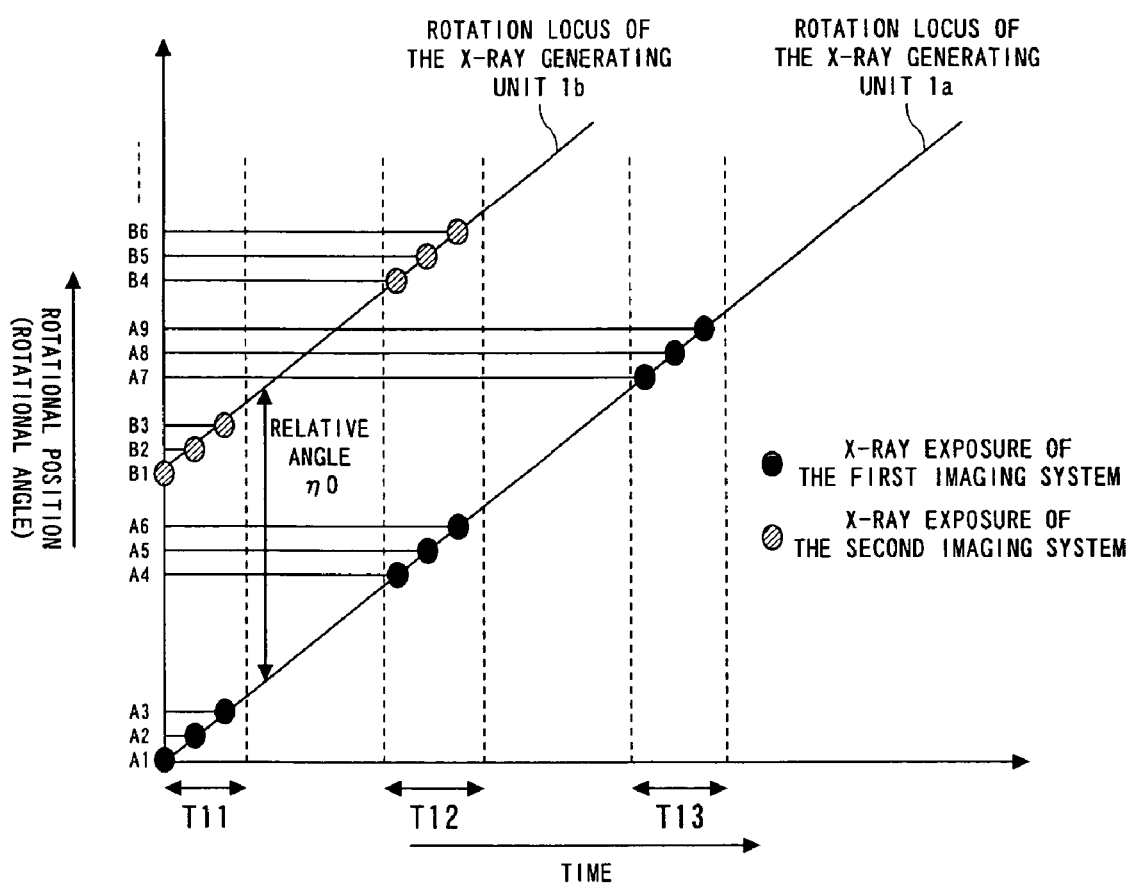
FIG. 9 is a diagram showing the relationship between palmic time-phase and the rotational positions of the X-ray generating units provided for the two imaging systems in FIG. 1 when the relative angle between the imaging systems is optimized.

FIG. 9 shows the rotational positions (vertical axis) of the X-ray generating units 1a and 1b with respect to time, i.e., the time-phase of the ECG signals (horizontal axis). For ease of explanation, it is assumed that each of the X-ray generating units 1a and 1b radiates X-rays at three different rotational positions at each of end-diastole times T11, T12, T13, . . . .

Figure 10:
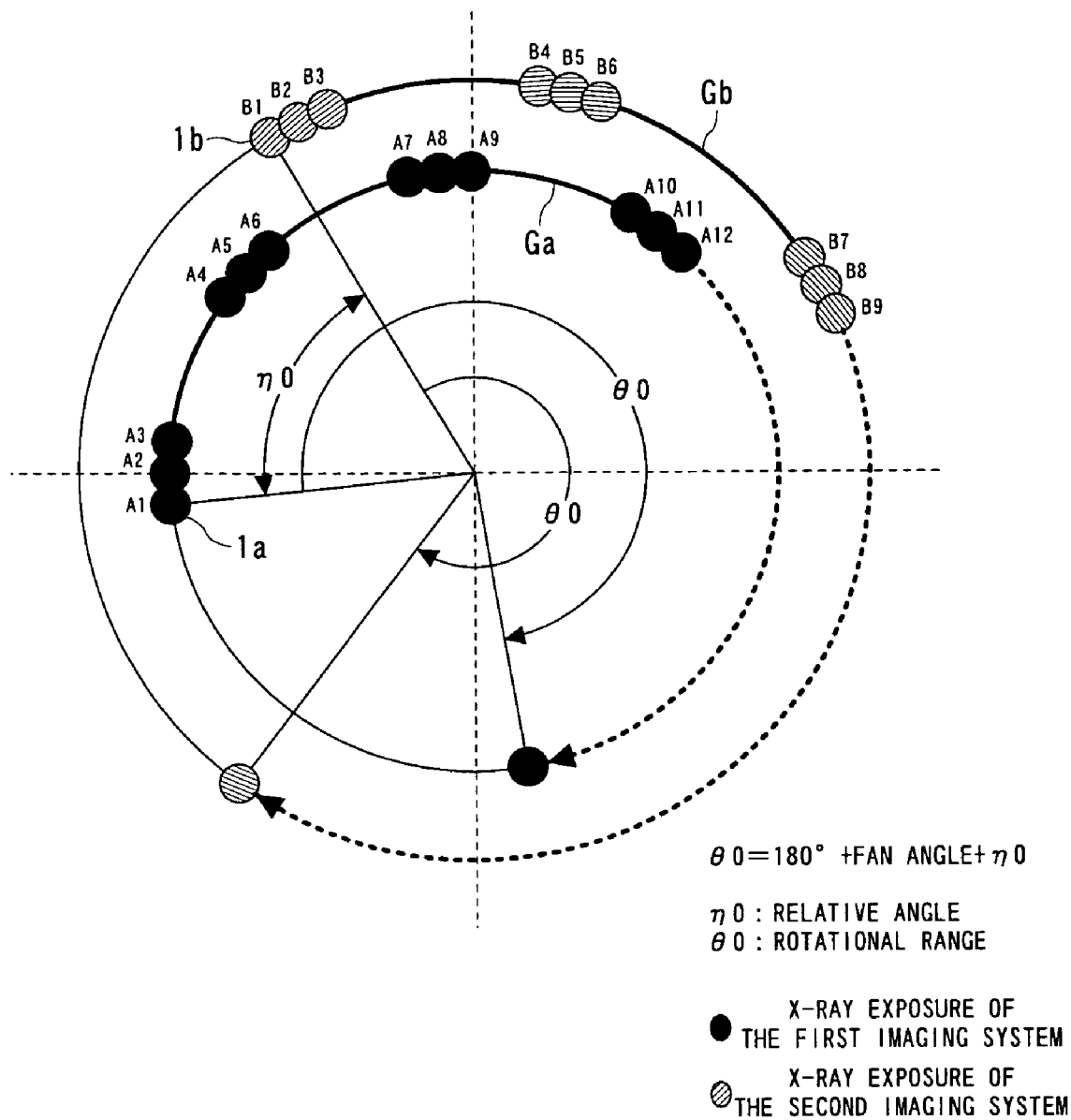
FIG. 10 is a diagram showing the rotational positions of the X-ray generating units of the two imaging systems in FIG. 1 when the relative angle between the imaging systems is optimized.

FIG. 10 relates to FIG. 9 and shows the rotational positions of the X-ray generating units 1a and 1b for radiating X-rays around the subject 150 (not shown). To make the explanation more easily understandable, FIG. 10 shows a case where the X-ray generating units 1a and 1b rotate along different circles Ga and Gb, respectively. Actually, the X-ray generating units 1a and 1b rotate along the same circle at the predetermined rotational velocity Vr.

Figure 17:
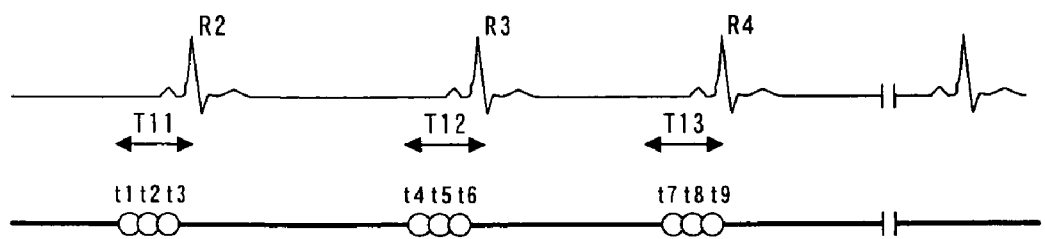
FIG. 17 is a diagram showing data collection timings in collecting projection data according to a conventional ECG gating method.
Figure 18:
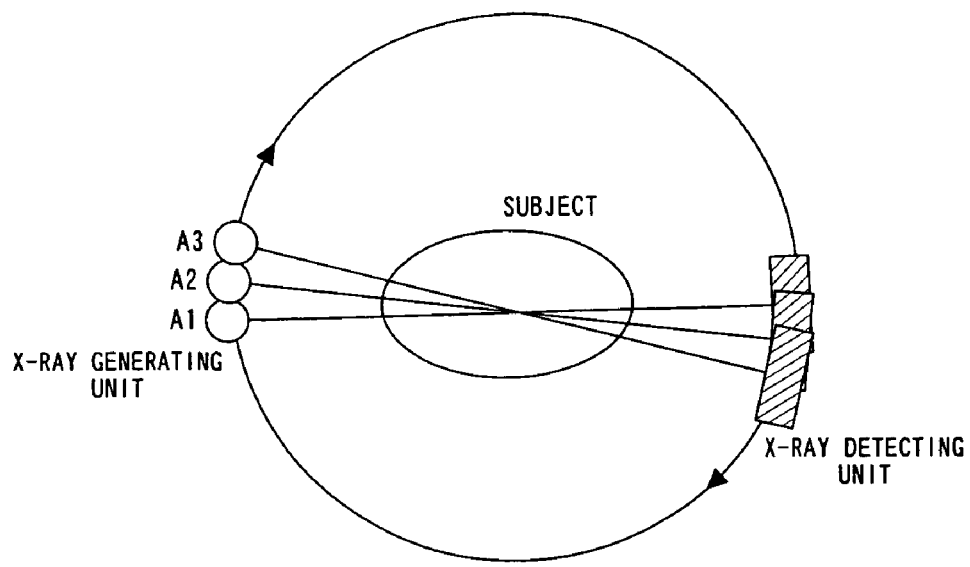
FIG. 18 is a diagram showing the positional relationship between an X-ray generating unit and an X-ray detecting unit in collecting projection data according to the conventional ECG gating method shown in FIG. 17.
Figure 19:
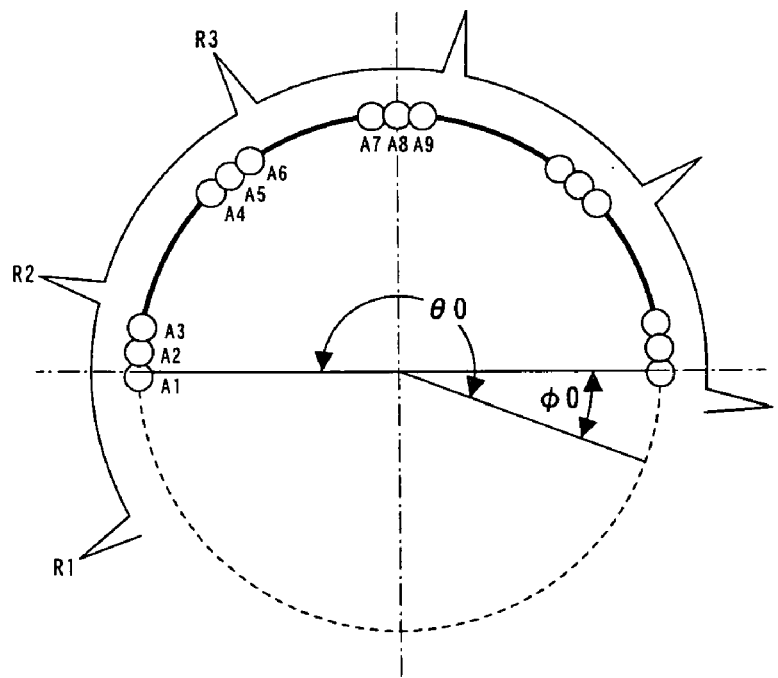
FIG. 19 is a diagram showing X-ray exposure positions in collecting projection data according to the conventional ECG gating method shown in FIG. 17.

As shown in FIGS. 9 and 10, when t=t1 (refer to FIG. 17) at end-diastole time T11, the X-ray generating unit 1a is located in a rotational position A1 and the X-ray generating unit 1b is located in a rotational position B1. The relative angle between the first and second imaging systems is set to the relative angle η0 calculated by the relative angle calculator 31 in the structure unit 3. While the relative angle η0 is being maintained, the X-ray generating unit 1a and the X-ray generating unit 1b are rotated such that timings t2 and t3 at end-diastole time T11 correspond to rotational positions A2 and A3 of the X-ray generating unit 1a and those B2 and B3 of the X-ray generating unit 1b, respectively, and timings t4 to t6 at end-diastole time T12 correspond to rotational positions A4 to A6 of the X-ray generating unit 1a and those B4 to B6 of the X-ray generating unit 1b, respectively.

It is preferable that the first imaging system be arranged as adjacent as possible to the second imaging system. Actually, interference occurs due to the size or shape of each of the X-ray generating units 1a and 1b, the X-ray detecting units 2a and 2b, and the holding members 5a and 5b. Therefore, the relative angle η0 between the imaging systems is generally set in the range of 50 to 90 degrees. According to the present embodiment, as shown in FIGS. 9 and 10, the relative angle η0 is set such that the rotational positions B1 to B3 of the X-ray generating unit 1b at end-diastole time T11 are arranged between the rotational positions A4 to A6 at end-diastole time T12 and those A7 to A9 at end-diastole time T13 of the X-ray generating unit 1a.

In this case, the X-ray generating unit 1b cannot be rotated between the rotational positions A3 and A4. Therefore, X-ray exposure of the X-ray generating unit 1a is interrupted at each of the rotational positions A1 to A3, thus maintaining the continuity of projection data obtained by the first and second imaging systems and preventing the subject 150 from being unnecessarily exposed to X-rays.

Since projection data is not collected between the rotational positions A3 and A4, it is necessary to increase the rotational range θ0 of each imaging system by an amount corresponding to the relative angle η0. Therefore, the rotational range θ0 of each imaging system is set such that the rotational range θ0 is equal to or more than (180 degrees+fan angle+relative angle η0) and is equal to or less than a settable maximum angle. The settable maximum angle is determined depending on the mechanical rotation stroke of the first imaging system and that of the second imaging system. For example, the rotational range θ0 is set to (180 degrees+fan angle+relative angle η0).

A method for calculating the relative angle η0 will now be described below. The calculation is performed by the relative angle calculator 31 in the structure unit 3. Assuming that Vr (degrees/second) denotes the rotational velocity of each of the first and second imaging systems and T0 (seconds) denotes the palmic cycle of the subject 150 and the respective values are supplied to the relative angle calculator 31, the relative angle η0 (degrees) can be calculated by the following Expression (1):

$$\eta 0 = \{(2n-1)/2\} \cdot Vr \cdot T0 \qquad (1)$$

where n is any integer.

As shown in FIG. 10, when the rotational positions B1 to B3 of the X-ray generating unit 1b at end-diastole time T11 are located between the rotational positions A4 to A6 of the X-ray generating unit 1a at end-diastole time T12 and those A7 to A9 thereof at end-diastole time T13, an integer n=2 in Expression (1). When the rotational positions B1 to B3 of the X-ray generating unit 1b at end-diastole time T11 are located between the rotational positions A1 to A3 of the X-ray generating unit 1a at end-diastole time T11 and those A4 to A6 thereof at end-diastole time T12, n=1 in Expression (1).

Figure 11:
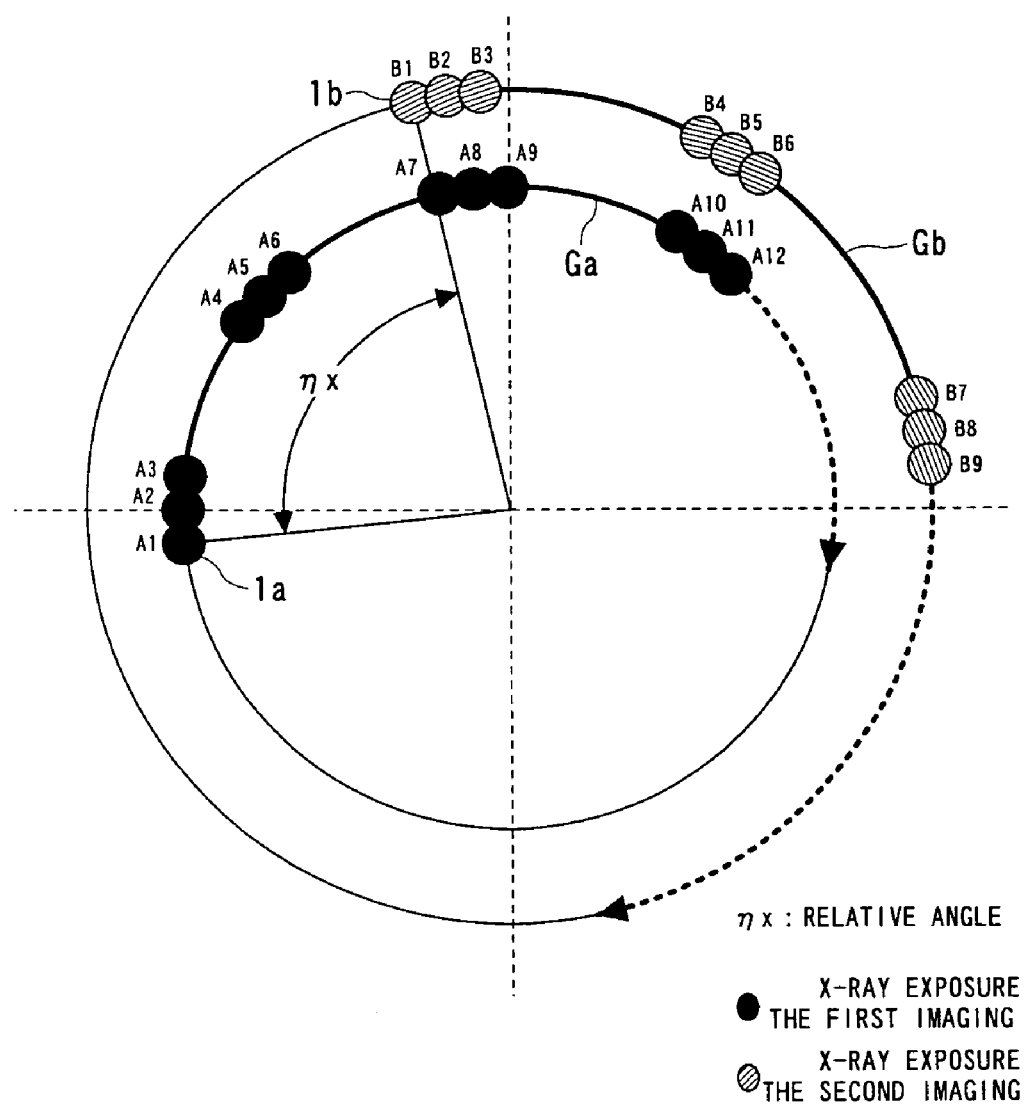
FIG. 11 is a diagram showing the rotational positions of the X-ray generating units provided for the respective imaging systems on condition that the relative angle between the two imaging systems in FIG. 1 is not optimized.

FIG. 11 is a diagram showing the rotational positions of the X-ray generating units 1a and 1b provided for the respective imaging systems on condition that the relative angle between the two imaging systems in FIG. 1 is not optimized.

In other words, FIG. 11 shows the rotational positions A1, A2, A3, ... of the X-ray generating unit 1a and those B1, B2, B3, ... of the X-ray generating unit 1b when projection data is collected using the first and second imaging systems having therebetween the relative angle ηx predetermined on the basis of, e.g., the average palmic cycle Tx of the subject 150, which is obtained just before imaging. If the palmic cycle T0 of the subject 150 obtained during imaging remarkably varies compared to the average palmic cycle Tx obtained just before imaging, the X-ray generating unit 1a and the X-ray generating unit 1b may generate X-rays at the same rotational position. It is, therefore, difficult to collect projection data at many angles with efficiency.

So long as the palmic cycle T0 of the subject 150 is not remarkably different from the average palmic cycle Tx, the relative angle ηx predetermined based on information regarding the palmic cycle Tx and the rotational velocity Vr of each imaging system can be used.

2. Generating Procedure of Image Data

Figure 12:
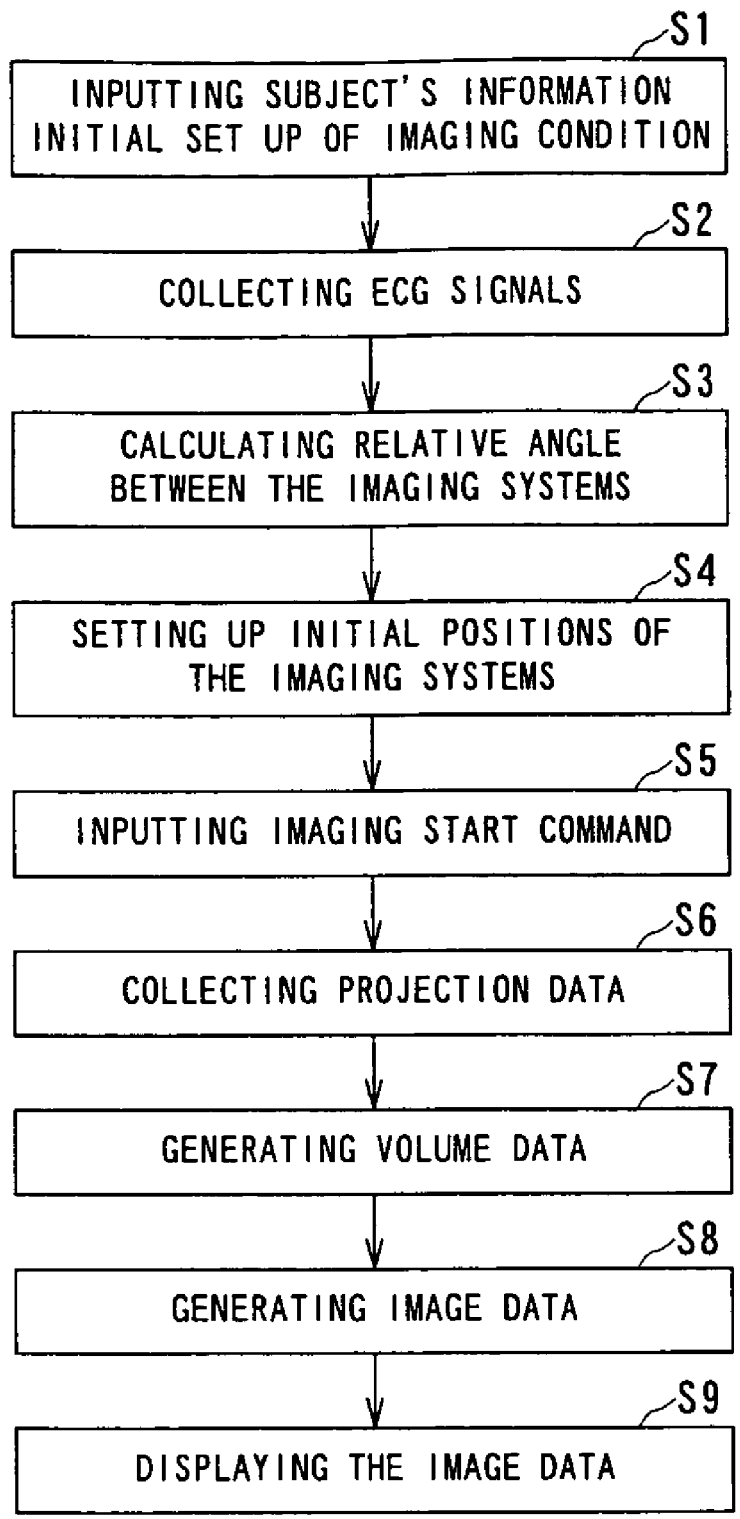
FIG. 12 is a flowchart of the process of generating image data through the X-ray diagnostic apparatus shown in FIG. 1.

Next, a process of generating image data in the X-ray diagnostic apparatus 100 according to the present embodiment will now be described below with reference to FIGS. 1 to 12. FIG. 12 is a flowchart of the process of generating image data through the X-ray diagnostic apparatus shown in FIG. 1.

Using the console 9, the operator inputs subject information regarding the subject 150 and performs initial setup of various imaging conditions, i.e., X-ray exposure conditions, the rotational velocity Vr of the first and second imaging systems, the imaging positions of the imaging systems relative to the body axis of the subject 150, and the rotational positions A1, A2, A3, ... of the X-ray generating unit 1a (step S1 of FIG. 12). Those set conditions are stored in the storage circuit of the system controller 11.

After the above initial setup is finished, the operator attaches electrodes of the ECG unit 10 to the chest of the subject 150. The ECG unit 10 converts ECG signals obtained from the subject 150 into digital signals and then supplies the digital signals to the system controller 11. The system controller 11 inputs the ECG signals and the rotational velocity Vr of the imaging systems set in the console 9 to the relative angle calculator 31 in the structure unit 3 (step S2 of FIG. 12).

The relative angle calculator 31 measures intervals between R waves or the palmic rate of the subject based on the ECG signals supplied from the ECG unit 10 to obtain the palmic cycle T0. Further, the relative angle calculator 31 calculates the relative angle η0 between the imaging systems using, e.g., Expression (1) on the basis of the palmic cycle T0 and the rotational velocity Vr (step S3 of FIG. 12).

Subsequently, the imaging system moving controller 32 in the structure unit 3 controls the imaging system moving devices 33a and 33b based on the relative angle η0 supplied from the relative angle calculator 31 and information regarding the rotational positions of the X-ray generating unit 1a supplied from the system controller 11 and then moves the X-ray generating units 1a and 1b to the rotational positions A1 and B1 shown in FIG. 9, respectively (step S4 of FIG. 12).

After the X-ray generating units 1a and 1b are set in the initial positions based on the palmic information of the subject 150, the operator inputs a command for starting X-ray imaging in the console 9. When a signal of the imaging start command is supplied to the system controller 11, X-ray imaging is started (step S5 of FIG. 12).

Subsequently, the system controller 11 detects first X-ray exposure timing t1 at end-diastole on the basis of the R wave R1 of the ECG signals of the subject 150 supplied from the ECG unit 10 subsequent to the imaging start command signal. Then, the system controller 11 performs X-ray exposure at X-ray exposure timing t1. In this instance, as described above with reference to FIG. 9, only the X-ray generating unit 1b is allowed to generate X-rays.

In X-ray imaging, the high-voltage control circuit 41 in the high-voltage generating unit 4 receives a drive signal supplied from the system controller 11 at the above-mentioned X-ray exposure timing t1. On the basis of the set X-ray exposure conditions, the high-voltage control circuit 41 controls the high-voltage generator 42 to apply high voltage to the X-ray tube 15 in the X-ray generating unit 1b. Subsequently, the X-ray tube 15 applies X-rays to the subject 150 through the X-ray beam limiting device 16. The X-rays, passed through the subject 150, are projected on the X-ray I. I. 21 in the X-ray detecting unit 2b, which is arranged opposite to the X-ray generating unit 1b with the subject 150 therebetween. The X-ray I. I. 21 transforms the X-rays passed through the subject 150 into an optical image. The X-ray TV camera 22 converts the optical image into electric signals (video signals). The A/D converter 23 converts the video signals, output from the X-ray TV camera 22 on a time series basis, into digital signals. The projection data storage circuit 71 in the image operation/storage unit 7 stores the digital signals.

On the other hand, the system controller 11 controls the imaging system moving controller 32 in the structure unit 3 to continuously rotate the first and second imaging systems about the subject 150 at the preset rotational velocity Vr. The system controller 11 supplies a drive signal for X-ray exposure to the high-voltage control circuit 41 in the high-voltage generating unit 4 at timing t=t2 when the X-ray generating unit 1a arrives at the predetermined rotational position A2.

In a manner similar to the case when t=t1, at end-diastole time T11, the X-ray generating unit 1b generates X-rays at the rotational positions B2 and B3 at timings t=t2 and t=t3, respectively. The X-ray detecting unit 2b detects projection data and then supplies the data to the projection data storage circuit 71 in the image operation/storage unit 7. The projection data storage circuit 71 stores the supplied data.

Subsequently, the system controller 11 allows the X-ray generating units 1a and 1b to generate X-rays at end-diastole time T12, which is determined on the basis of the ECG signals supplied from the ECG unit 10. In other words, when the X-ray generating units 1a rotating at the rotational velocity Vr arrives at each of the rotational positions A4 to A6 preset at end-diastole time T12 and the X-ray generating unit rotating 1b rotating at the rotational velocity Vr arrives at each of the corresponding rotational positions B4 to B6 similarly preset, the system controller 11 supplies a drive signal for X-ray exposure to the high-voltage control circuit 41 in the high-voltage generating unit 4, thus allowing the X-ray generating units 1a and 1b to radiate X-rays. The X-ray detecting units 2a and 2b detect projection data obtained by X-ray exposure and supply the data to the projection data storage circuit 71. The projection data storage circuit 71 stores the supplied data.

In this manner, the system controller 11 allows the X-ray generating units 1a and 1b to generate X-rays at end-diastole times T13, T14, . . . , which are determined on the basis of R waves R3, R4, . . . of the ECG signals supplied from the ECG unit 10. The projection data storage circuit 71 stores projection data obtained by the X-ray detecting units 2a and 2b.

Projection data is continuously collected until the rotational range θ0 of each of the X-ray generating units 1a and 1b is equivalent to (at least 180 degree+fan angle+relative angle η0) (step S6 of FIG. 12).

In addition to pieces of projection data collected while the first and second imaging systems are being rotated, the projection data storage circuit 71 stores pieces of information regarding the rotational positions of the X-ray generating units 1a and 1b on collecting the projection data such that each piece of projection data is related to the corresponding piece of information regarding the rotational position.

If the collection and the storage of projection data within the rotational range θ0 are completed according to the above-mentioned process, the image operation circuit 72 in the image operation/storage unit 7 performs a convolution process using the projection data and the rotational position information stored in the projection data storage circuit 71. Further, the projection data subjected to the convolution process is back projected on predetermined lattice points in a three-dimensional lattice, which is virtually set in the region of interest of the subject 150, thus generating volume data in the region of interest. The image data storage circuit 73 stores the generated volume data (step S7 of FIG. 12). A method for generating volume data based on projection data collected by an X-ray detecting unit having two-dimensional detecting elements is known as an image reconstruction technique for X-ray CT apparatuses. Accordingly, a detailed description of the method will be omitted.

Subsequently, the image operation circuit 72 generates desired three-dimensional or two-dimensional image data on the basis of the volume data generated as mentioned above in accordance with an image display mode, which the operator selects in the console 9. The image data storage circuit 73 temporarily stores the generated image data (step S8 of FIG. 12).

The system controller 11 reads image data corresponding to the preset image display mode from the image data storage circuit 73 and allows the monitor 83 of the display unit 8 to display the image data. In other words, the system controller 11 reads desired image data stored in the image data storage circuit 73 and supplies the read image data to the display data generating circuit 81 in the display unit 8. The display data generating circuit 81 combines the image data supplied from the image data storage circuit 73 with attached information regarding subject information or the imaging conditions supplied from the system controller 11, thus generating display image data. The conversion circuit 82 performs the D/A conversion and the TV (Television) format conversion to the display image data to generate video signals. The monitor 83 displays the generated video signals (step S9 of FIG. 12).

According to the present embodiment, image reconstruction is performed using projection data collected in palmic time-phase at end-diastole or end-systole at which the motion of the heart of the subject is relatively small. Thus, the influence of the pulsating motion can be reduced. In addition, the two imaging systems arranged with the predetermined relative angle therebetween are rotated about the subject to collect X-ray projection data, thus, the data can be collected for a short time.

According to the present embodiment, the relative angle between the two imaging systems is set on the basis of palmic information of the subject and the rotational velocity. Thus, projection data in the palmic time-phase can be collected at many angles without duplication. The obtained projection data is subjected to the reconstruction process, thus generating high-quality X-ray image data.

Having described the preferred embodiment of the present invention, it should be understood that the present invention is not limited to the above-mentioned embodiment but many modifications and variations are possible within the scope of the invention. For example, according to the above-mentioned embodiment, the relative angle between the imaging systems is optimized on the basis of the palmic cycle obtained by ECG signals of the subject and the rotational velocity of the imaging systems. The rotational velocity Vr of the imaging systems also can be set on the basis of the preset relative angle η0 between the imaging systems and the palmic cycle T0 of the subject. In this instance, the rotational velocity Vr can be obtained by the following Expression (2) which is obtained by modifying Expression (1):

$$Vr = \{2/(2n-1)\} \cdot (\eta 0/T0) \quad (2)$$

where n is any integer.

The expression for calculating the relative angle η0 between the imaging systems and that for calculating the rotational velocity Vr are not limited to Expressions (1) and (2).

The above-mentioned embodiment relates to the collection of projection data using the two imaging systems. Three or more imaging systems can also be used. The present invention can be applied to a system using a plurality of X-ray generating units, such as a stereo tube or a flying focal spot. Although the focal interval of a common stereo tube is generally fixed, a stereo tube with a variable focal interval can also be used. The flying focal spot is a technique used in an X-ray CT apparatus. Generally, the distance between two focal points is approximately 1 mm. When the present embodiment uses the flying focal spot technique, preferably, the distance between the focal points is in the range of 5 to 20 cm.

Furthermore, according to the present embodiment, FIG. 10 shows the case where the rotational positions B1 to B3 of the X-ray generating unit 1b at end-diastole time T11 are arranged between the rotational positions A4 to A6 of the X-ray generating unit 1a at end-diastole time T12 and those A7 to A9 thereof at end-diastole time T13. The arrangement is not limited to the above.

Figure 13:
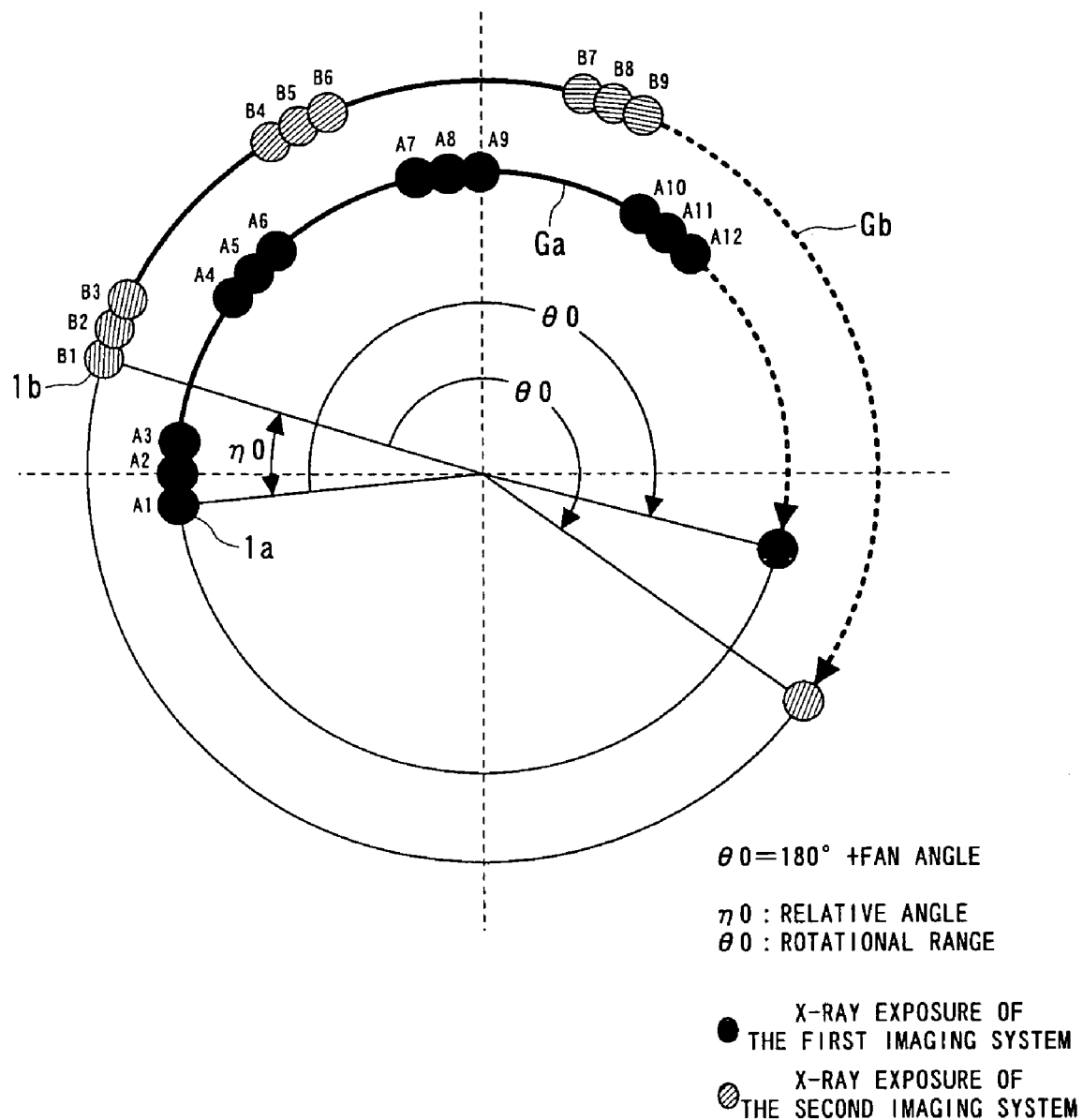
FIG. 13 is a diagram showing an example of another arrangement of the rotational positions of the two X-ray generating units when the two imaging systems shown in FIG. 1 have the optimized relative angle therebetween.

FIG. 13 is a diagram showing an example of another arrangement of the rotational positions of the two X-ray generating units when the two imaging systems shown in FIG. 1 have the optimized relative angle therebetween.

For example, when the relative angle between the imaging systems is set to a small angle as shown in FIG. 13, the rotational positions B1 to B3 of the X-ray generating unit 1b at end-diastole time T11 can be arranged between the rotational positions A1 to A3 of the X-ray generating unit 1a at end-diastole time T11 and those A4 to A6 thereof at end-diastole time T12. The rotational positions B1 to B3 of the X-ray generating unit 1b at end-diastole time T11 can also be set between the rotational positions of the X-ray generating unit 1a at end-diastole time T13 and those at the following end-diastole time. For example, when each imaging system uses a microminiaturized X-ray generating unit, the relative angle between the imaging systems can be reduced to approximately 5 degrees. In this case, the X-ray generating unit 1a located in each of the rotational positions A1 to A3 applies X-rays to the subject together with the X-ray generating unit 1b located in the corresponding rotational position, the rotational positions A1 to A3 corresponding to those B1 to B3, respectively. In this instance, the rotational range of each imaging system is set such that the rotational range is equal to (180 degrees+fan angle).

Furthermore, projection data can be collected in the rotational positions A1 to A3 in FIG. 10. In this case, although the image quality of obtained image data is slightly deteriorated, the amount of x-rays applied to the subject 150 can be reduced because the rotational range of each imaging system is equal to (180 degrees+fan angle).

In addition, the relative angle therebetween can be set by changing rotation start timings of the two imaging systems.

Figure 14:
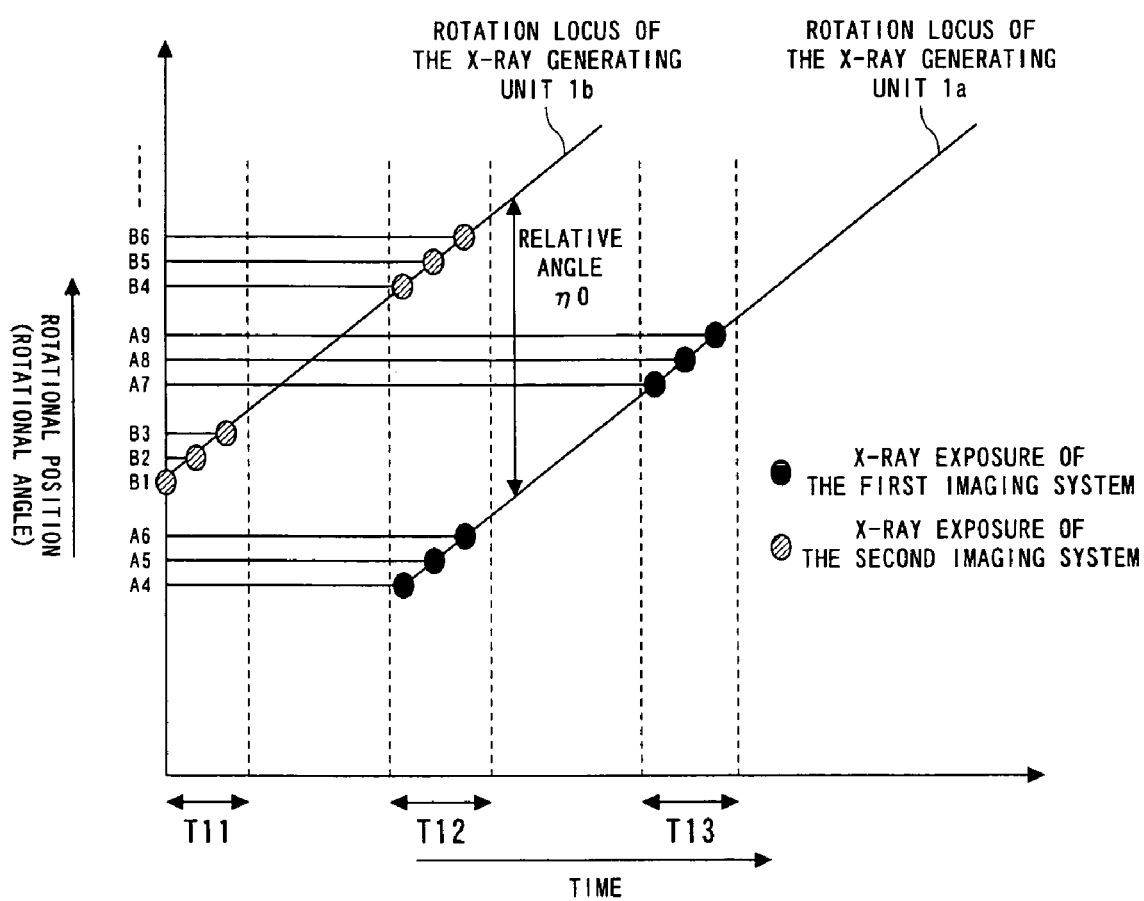
FIG. 14 is a diagram showing the relationship between the rotational positions of the X-ray generating units of the two respective imaging systems in FIG. 1 and palmic time-phase when the rotation loci of the imaging systems and the relative angle therebetween are optimized by changing the rotation start timings of the imaging systems.
Figure 15:
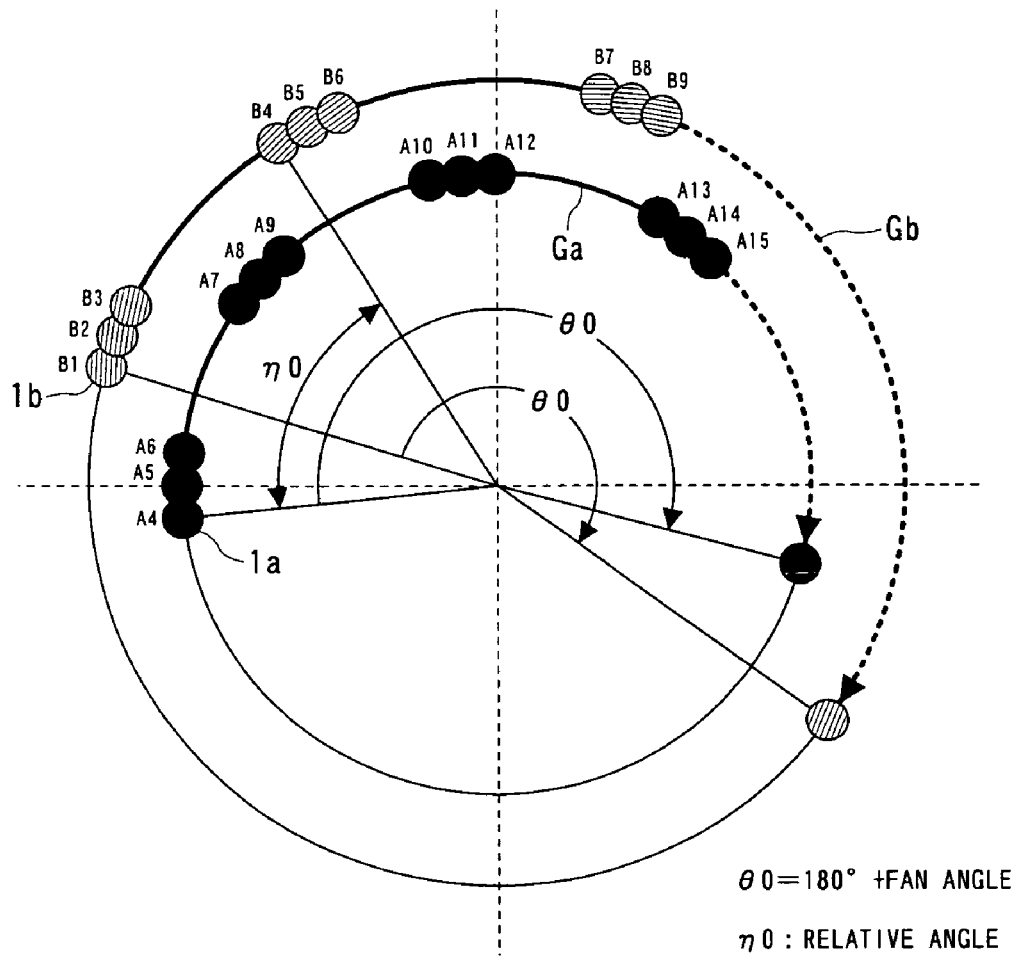
FIG. 15 is a diagram showing the rotational positions of the X-ray generating units of the two imaging systems in FIG. 14.

FIG. 14 is a diagram showing the relationship between the rotational positions of the X-ray generating units of the two respective imaging systems in FIG. 1 and palmic time-phase when the rotation loci of the imaging systems and the relative angle therebetween are optimized by changing the rotation start timings of the imaging systems. FIG. 15 is a diagram showing the rotational positions of the X-ray generating units of the two imaging systems in FIG. 14.

As shown in FIGS. 14 and 15, rotation start timings of the two imaging systems are changed such that the timings are different from each other. Thus, the relative angle can be arbitrarily set. For example, in palmic time-phase T11, the first imaging system is stopped and only the second imaging system is rotated. X-ray exposure and X-ray detection are performed by the second imaging system alone.

Before data is collected in palmic time-phase T12 at the latest, e.g., at timing t4 serving as data collection timing, the rotation of the first imaging system is started. After palmic time-phase T12, X-ray exposure and X-ray detection are performed using both of the first and second imaging systems.

When the first and second imaging systems are controlled by the imaging system moving devices 33a and 33b as mentioned above, the redundant rotations of the first and second imaging systems can be reduced and the relative angle η0 can be arbitrarily set during rotation. Consequently, more pieces of spatially continuous data can be collected in the smaller rotational ranges θ0 of the imaging systems.

The relative angle between the imaging systems can be set by changing rotation end timings in addition to the rotation start timings.

Alternatively, the relative angle therebetween can be set by changing only the rotation end timings while the rotations of the two imaging systems are started at the same timing.

Therefore, when the amount of shift between the rotation start timings of the two imaging systems is the same as that between the rotation end timings thereof, the rotational ranges θ0 of the imaging systems are equal as shown in FIG. 15. In addition, the rotational ranges θ0 thereof can be different from each other.

Next, a method for controlling the imaging systems to optimize the data collection range will now be described below.

Figure 16:
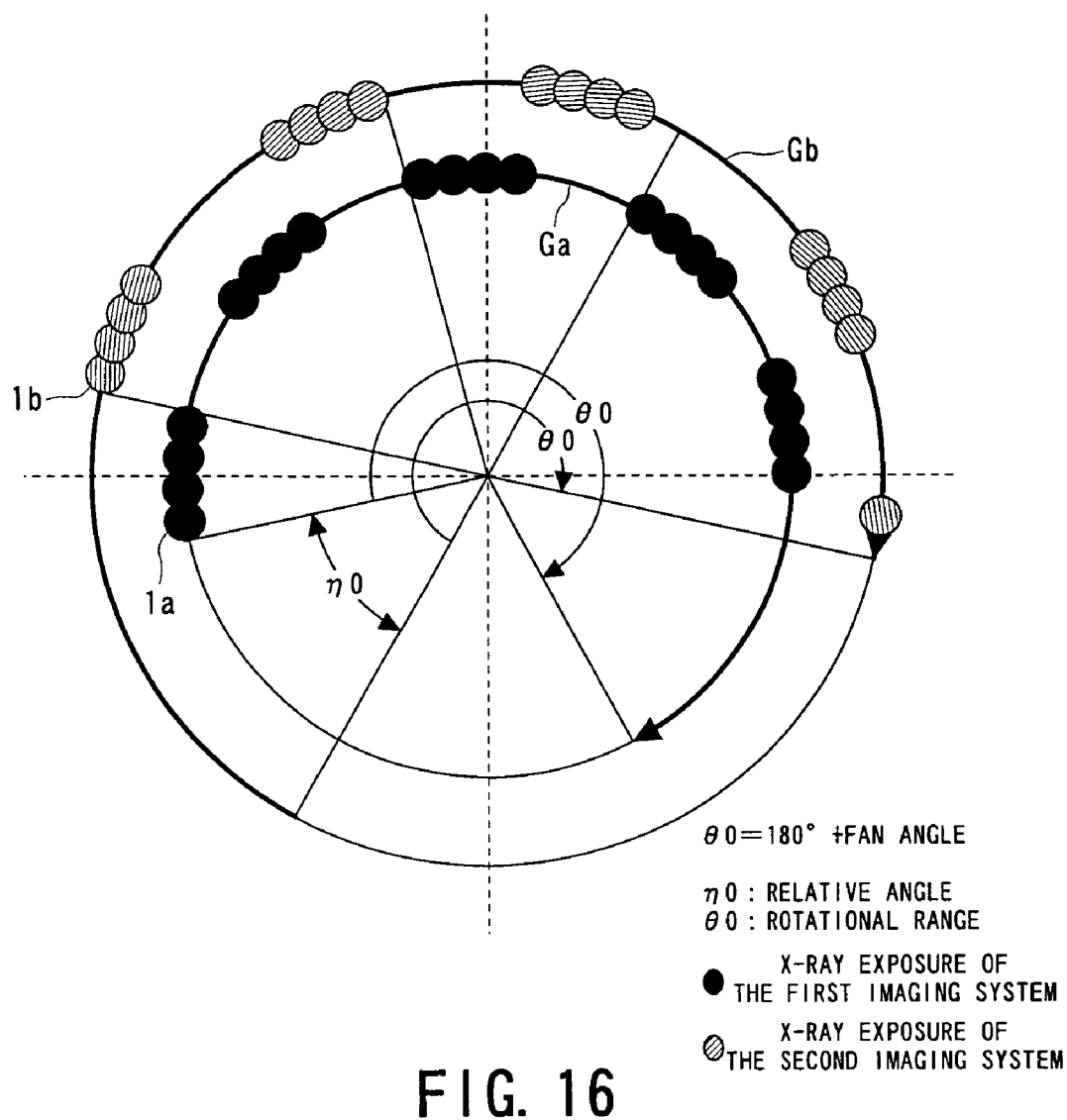
FIG. 16 is a diagram showing the rotational positions of the X-ray generating units in a case where the data collection range is optimized while controlling the rotations of the two imaging systems in FIG. 1 is being made easier.

FIG. 16 is a diagram showing the rotational positions of the X-ray generating units in a case where the data collection range is optimized while controlling the rotations of the two imaging systems in FIG. 1 is being made easier.

Referring to FIG. 16, the rotations of the two imaging systems are set such that the rotation start timing of the first imaging system is substantially the same as that of the second imaging system and the rotation end timing of the first imaging system is substantially the same as that of the second imaging system. Therefore, the rotations of the two imaging systems are simultaneously started and the imaging systems are rotated while the constant relative angle η0 therebetween is being maintained. When the rotation start timing of the first imaging system is set to be the same as that of the second imaging system and the rotation end timing of the first imaging system is set to be the same as that of the second imaging system as mentioned above, the imaging systems can be easily controlled. In this case, the rotational ranges θ0 of the respective imaging systems overlap with each other in an area and they do not overlap with each other in the other area.

By the way, angles at which data necessary for imaging is collected correspond to an angular range obtained by adding the fan angle to 180 degrees in many cases. Therefore, when an imaging region is set so that the rotational angle of each imaging system is equal to or larger than (180 degrees+fan angle) and data collection is not performed outside the imaging region, the number of X-ray exposure times and the amount of X-ray exposure can be reduced. It results in a reduction in the amount of X-rays applied to the subject.

Therefore, the imaging system moving devices 33a and 33b controls the imaging systems such that the respective imaging systems are rotated in a range which covers at least the imaging region. In this case, sufficiency can be obtained if the area where the rotational ranges θ0 of the two imaging systems overlap with each other cover the imaging region. For example, the rotational ranges θ0 of the two imaging systems are set such that the area where the rotational ranges θ0 thereof overlap with each other corresponds to the imaging region as shown in FIG. 16.

On the other hand, the X-ray exposure and the x-ray detection are performed only in the imaging region. The X-ray exposure and the x-ray detection are not performed in the rotational ranges θ0 excluding the imaging region. In other words, since one imaging system located in the overlapped rotational range θ0 at the rotation start timing is positioned in the imaging region upon starting the rotation, the imaging system performs the X-ray exposure and the X-ray detection. The other imaging system performs the X-ray exposure and the X-ray detection after it enters the overlapped rotational range θ0, i.e., the imaging region.

On the contrary, when one imaging system, which has generated X-rays and detected X-rays first, enters the area where the rotational ranges θ0 of the two imaging system do not overlap with each other, i.e., it leaves the imaging region, the imaging system is controlled to stop the X-ray exposure and the X-ray detection. At that time, the rotational range θ0 of the other imaging system overlaps with the other rotational range up to the end point, i.e., it is located within the imaging region, the imaging system generates X-rays and detects X-rays up to the rotation end point.

When the rotational positions and the data collection positions of the two imaging systems are controlled as mentioned above, continuous data can be collected at angles of (180 degrees+fan angle) with easy control. Thus, image quality can be increased.

In the imaging region, there are gaps between the data collection positions of the two imaging systems. When data is collected in positions opposite to the data collection positions and the collected data is used for imaging, a deterioration of image quality caused by the gaps between the data collection positions can be reduced.

It is preferable to set the relative angle η0 depending on palmic rate as mentioned above. In the example shown in FIG. 16, each imaging system collects data four times in each palmic time-phase. In this case, the X-ray exposure timings of the respective imaging systems may be different from each other.

In the above-mentioned embodiment, the X-ray detecting units 2a and 2b each having the X-ray I. I. 21 have been described. When X-ray detecting units each having a planar X-ray detector (2-dimensional array type X-ray detector 50) are used, the same advantages can be obtained. According to the above-mentioned embodiment, ECG signals are collected to obtain palmic information of the subject. Other biological information, such as a curve indicating a change in cardiac volume of the left ventricle shown in FIG. 8, can be used.

In addition, the above-mentioned embodiment relates to the case where projection data is subjected to the image reconstruction process to obtain volume data and the volume data is subjected to the volume rendering process to generate three-dimensional image data or two-dimensional image data, such as MIP image data or MPR image data. The present invention is not limited to the above case.

On the other hand, a period during which X-ray exposure is performed is not limited to end-diastole. X-ray exposure can also be performed at end-systole. In this case, the number of X-ray exposure times is not limited to three times at end-diastole or end-systole. Furthermore, the above-mentioned embodiment relates to the case where X-ray exposure is performed at only end-diastole or end-systole. The present invention can be applied to the following case: While the imaging systems are being rotated, X-rays are generated at regular intervals to obtain projection data, projection data obtained at end-diastole times is selected, and the selected projection data is subjected to the reconstruction process. In this case, although the amount of X-rays applied to the subject is increased, advantageously, a method for controlling X-ray exposure can be simplified.

According to the above-mentioned embodiment, the relative angle calculator 31 in the structure unit 3 can update the relative velocity of the imaging systems in accordance with a change in palmic information which is supplied from the ECG unit 10. Therefore, even if the palmic cycle of the subject 150 varies during imaging, projection data can be collected without duplication. Similarly, when the rotational velocity of the imaging systems is updated in accordance with a change in palmic information during imaging, projection data can also be collected without duplication.

What is claimed is:

1. An X-ray diagnostic apparatus comprising:
a palmic information collecting unit collecting a palmic information of a subject;
imaging units irradiating and detecting X-rays respectively to the subject on a predetermined time-phase of the palmic information to collect projection data;
an imaging system moving unit moving the imaging units respectively around the subject;
an imaging system motion control unit controlling motions of the imaging units respectively by setting up a relative angle formed by the imaging units according to the palmic information; and
an image data generating unit performing a reconstruction process to the projection data to generate X-ray image data.

2. An X-ray diagnostic apparatus according to claim 1, wherein the imaging system motion control unit is configured to set up moving velocities of the imaging units respectively according to the palmic information.

3. An X-ray diagnostic apparatus according to claim 1, wherein the imaging system motion control unit is configured to set up moving ranges of the imaging units to 180 degrees+fan angles of the imaging units+the relative angle formed by the imaging units and above respectively.

4. An X-ray diagnostic apparatus according to claim 1, wherein the imaging system motion control unit is configured to set up the relative angle formed by the imaging units to five degrees and above and ninety degree and under.

5. An X-ray diagnostic apparatus according to claim 1, wherein the imaging units are configured to move with a same velocity substantially around the subject.

6. An X-ray diagnostic apparatus according to claim 1, wherein the imaging units are configured to collect the projection data at either an end of a systole and an end of a diastole on the palmic information.

7. An X-ray diagnostic apparatus according to claim 1, wherein the imaging units include two-dimensional X-ray detectors and the image data generating unit is configured to generate volume data by performing the reconstruction process to the projection data collected with the two-dimensional X-ray detectors.

8. An X-ray diagnostic apparatus according to claim 1, wherein the palmic information collecting unit is configured to collect ECG signals of the subject as the palmic information.

9. An X-ray diagnostic apparatus according to claim 1, wherein the imaging system motion control unit is configured to set up the relative angle formed by the imaging units by changing at least one side of move start timings and move end timings of the imaging units.

10. An X-ray diagnostic apparatus according to claim 1, wherein the imaging system motion control unit is configured to set up each move start timing and each move end timings of the imaging units identically substantially.

11. An X-ray diagnostic apparatus according to claim 1, wherein the imaging units are configured to irradiate and detect the X-rays only on imaging area setup as 180 degrees+fan angles of the imaging units and above within moving ranges of the imaging units.

12. An X-ray diagnostic apparatus comprising:
imaging units irradiating and detecting X-rays respectively to a subject to collect projection data;
an imaging system moving unit moving the imaging units respectively with a same velocity substantially around the subject;
an imaging system motion control unit changing a relative angle formed by the imaging units according to the same velocity while the imaging units are moving; and
an image data generating unit performing a reconstruction process to the projection data to generate X-ray image data.

13. An X-ray diagnostic apparatus according to claim 12, wherein the imaging units is configured to collect the projection data at unoverlapping ranges each other.

14. An X-ray imaging method comprising:
collecting a palmic information of a subject;
setting up a relative angle formed by imaging units arranged around the subject according to the palmic information and moving velocities of the imaging units;
collecting projection data at a predetermined time-phase on the palmic information, moving the imaging units around the subject; and
performing a reconstruction process to the projection data to generate X-ray image data.

* * * * *